US008600468B2

(12) United States Patent
Yamamoto et al.

(10) Patent No.: US 8,600,468 B2
(45) Date of Patent: Dec. 3, 2013

(54) BIOMETRIC INFORMATION MEASURING APPARATUS AND BIOMETRIC INFORMATION MEASURING SYSTEM

(75) Inventors: Koji Yamamoto, Kawanishi (JP); Satoshi Yokota, Toyonaka (JP); Yoshiroh Nagai, Nishinomiya (JP); Kazumi Kitajima, Higashiosaka (JP); Norihiro Tateda, Sakai (JP)

(73) Assignee: Konica Minolta Sensing, Inc. (JP)

( * ) Notice: Subject to any disclaimer, the term of this patent is extended or adjusted under 35 U.S.C. 154(b) by 1375 days.

(21) Appl. No.: 12/006,400

(22) Filed: Jan. 2, 2008

(65) Prior Publication Data

US 2008/0243393 A1 Oct. 2, 2008

(30) Foreign Application Priority Data

Jan. 9, 2007 (JP) .................. 2007-001705

(51) Int. Cl.
*A61B 5/1455* (2006.01)

(52) U.S. Cl.
USPC ............................ 600/323; 600/310; 600/324

(58) Field of Classification Search
USPC ................................ 600/309–344
See application file for complete search history.

(56) References Cited

U.S. PATENT DOCUMENTS

| | | | |
|---|---|---|---|
| 5,519,380 A | 5/1996 | Edwards | |
| 5,724,025 A * | 3/1998 | Tavori | 340/573.1 |
| 6,198,394 B1 | 3/2001 | Jacobsen et al. | |
| 6,513,532 B2 | 2/2003 | Mault et al. | 128/921 |
| 6,607,484 B2 | 8/2003 | Suzuki et al. | 600/300 |
| 2002/0111541 A1* | 8/2002 | Bibl et al. | 600/300 |
| 2003/0065257 A1 | 4/2003 | Mault et al. | 600/407 |
| 2004/0059205 A1 | 3/2004 | Carlson et al. | 600/310 |
| 2005/0246295 A1* | 11/2005 | Cameron | 705/412 |
| 2006/0099969 A1 | 5/2006 | Staton et al. | |
| 2007/0073178 A1* | 3/2007 | Browning et al. | 600/519 |

FOREIGN PATENT DOCUMENTS

| | | |
|---|---|---|
| EP | 2022394 A1 | 2/2009 |
| GB | 2425669 A | 11/2006 |
| JP | 10-305016 A | 11/1998 |
| JP | 2001-344352 A | 12/2001 |
| JP | 2002-297870 A | 10/2002 |
| JP | 2004-509652 A | 4/2004 |
| JP | 2005-538784 A | 12/2005 |

OTHER PUBLICATIONS

Japanese Notice of Reasons for Rejection dated Aug. 9, 2011, for counterpart Japanese Application No. 2007-001705, together with an English translation thereof.
Partial European Search Report for Application No./Patent No. 08000154.8-1526/1943943, dated Sep. 26, 2012.
Extended European Search Report for Application No. 08000154.8-1526/1943943, dated Dec. 13, 2012.

* cited by examiner

*Primary Examiner* — Eric Winakur
*Assistant Examiner* — Marjan Fardanesh
(74) *Attorney, Agent, or Firm* — Cantor Colburn LLP

(57) ABSTRACT

A biometric information measuring apparatus has a storage device for storing data concerning a biometric signal or biometric information derived from the biometric signal in association with position information indicating the current location of a sensor unit of the apparatus. Since the biometric information measuring apparatus provides the position information acquired when the data on the biometric signal or the biometric information was obtained, one can know the location and behavior of a subject at the time of measurement and exactly analyze the biometric information on the subject.

7 Claims, 22 Drawing Sheets

(PHOTOPLETHYSMOGRAPHIC SIGNAL)

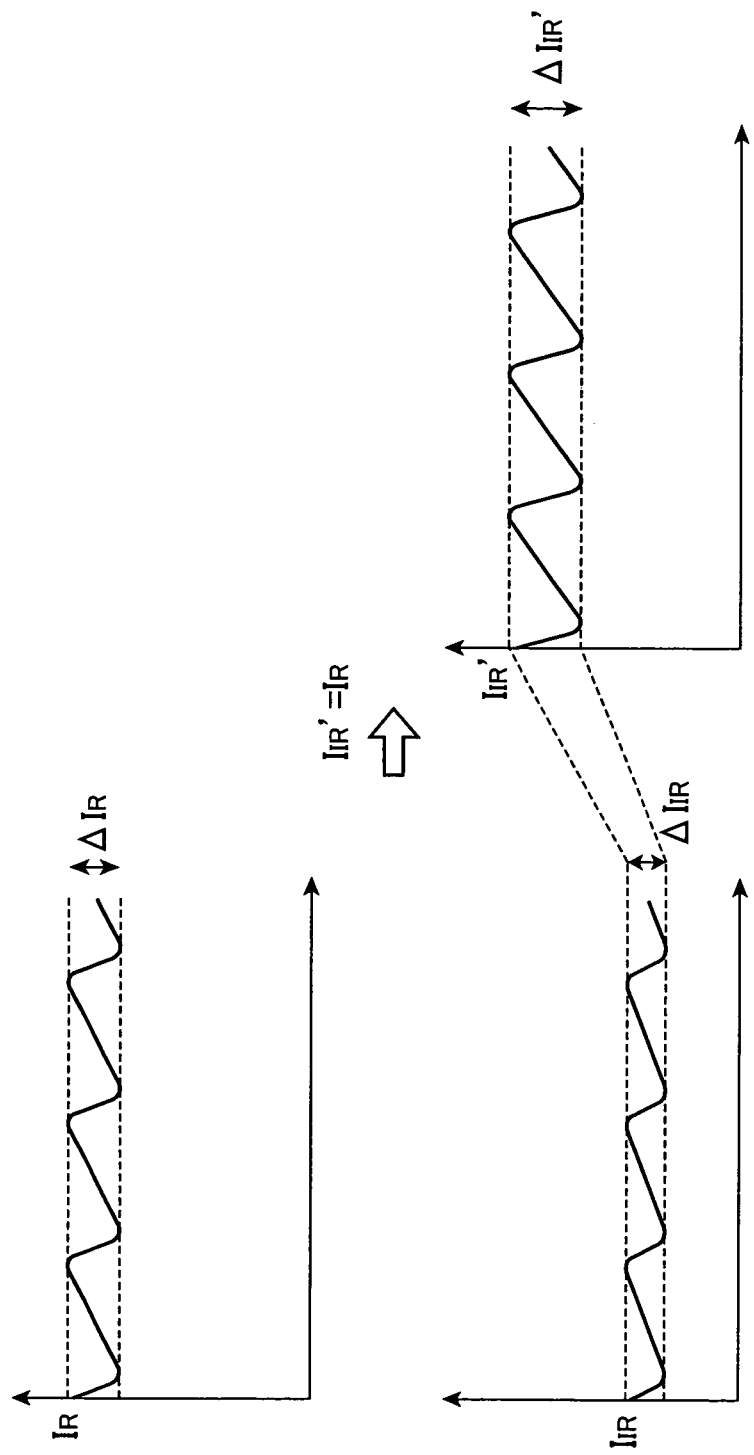

FIG.11
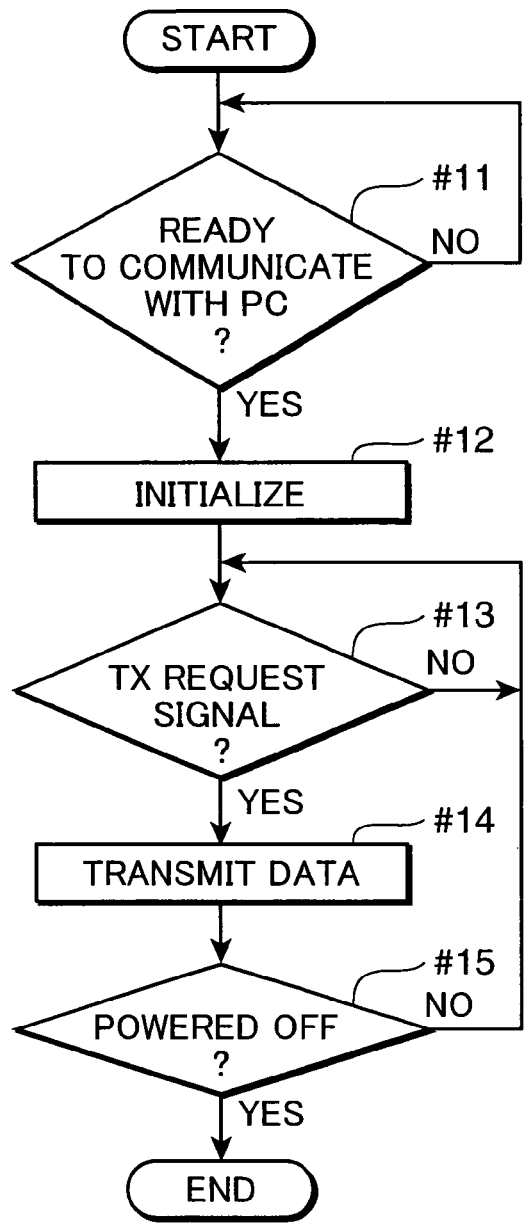
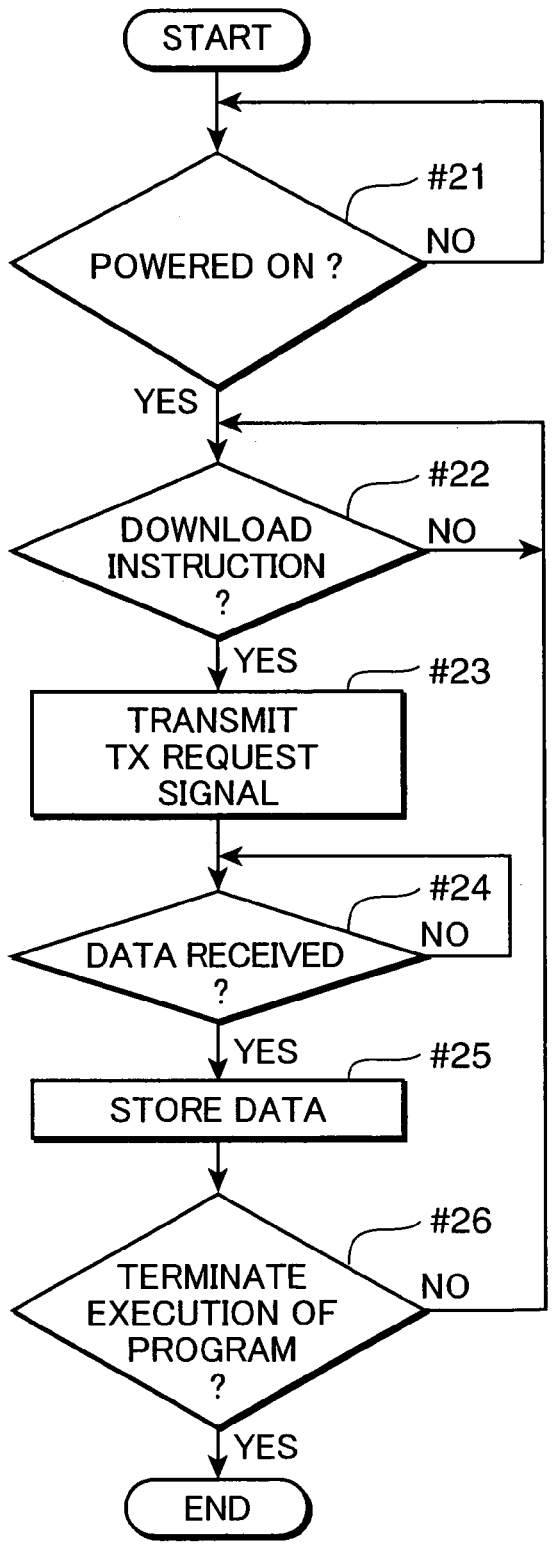

US 8,600,468 B2

BIOMETRIC INFORMATION MEASURING APPARATUS AND BIOMETRIC INFORMATION MEASURING SYSTEM

This application is based on Japanese Patent Application No. 2007-001705 filed on Jan. 9, 2007, the contents of which are hereby incorporated by reference.

BACKGROUND OF THE INVENTION

1. Field of the Invention

The present invention relates to a biometric information measuring apparatus and a biometric information measuring system for measuring biometric information, such as arterial oxygen saturation and heart rate.

2. Description of the Related Art

A pulse oximeter is a device often used in diagnosing sleep apnea syndrome (SAS) or chronic obstructive pulmonary disease (COPD), for instance. The pulse oximeter has a sensor unit which is attached to a specified body part of a subject. The sensor unit emits light toward the body part and detects part of the light reflected from or passing through the body part. The pulse oximeter is configured to measure blood oxygen saturation ($SpO_2$) based on the amount of light detected by the sensor unit.

When connected to a personal computer in which a specific program is installed, the pulse oximeter can communicate therewith. In this case, the personal computer receives data on oxygen saturation during sleep for one night from the pulse oximeter attached to the subject and calculates changes in the oxygen saturation and the severity of sleep apnea in terms of oxygen desaturation index (ODI) which is defined as an average number of oxygen desaturation episodes per unit time of sleep obtained by averaging the received data.

Japanese Unexamined Patent Publication No. 2005-538784 describes an arrangement for measuring and monitoring the state of a cardiovascular system of a subject by using an electrocardiogram (ECG) measuring configuration. According to the Publication, the ECG measuring configuration transmits measurement data on the state of the cardiovascular system together with information on the location of the subject determined by use of the Global Positioning System (GPS) to a medical expert.

Generally, a biometric state of a human being monitored varies depending on his or her behavior and location, such as whether the subject is currently sleeping, bathing or walking, for instance. Therefore, it would be possible to analyze biometric information more exactly if the behavior and location of the subject at the time of measurement are known.

SUMMARY OF THE INVENTION

In light of the foregoing, it is an object of the present invention to provide a biometric information measuring apparatus and a biometric information measuring system which make it possible to analyze biometric information more exactly.

According to a biometric information measuring apparatus and a biometric information measuring system of the invention, data concerning a biometric signal or biometric information derived from the biometric signal is stored in a storage device in association with position information. Therefore, the biometric information measuring apparatus and the biometric information measuring system provide the biometric signal or the biometric information together with the position information acquired when the data on the biometric signal or the biometric information was obtained. The position information provided by the biometric information measuring apparatus or system makes it possible to know the location and behavior of a subject at the time of measurement so that one can exactly analyze the biometric information on the subject.

These and other objects, features and advantages of the invention will become more apparent upon a reading of the following detailed description along with the accompanying drawings.

BRIEF DESCRIPTION OF THE DRAWINGS

FIG. 6 is a diagram for explaining normalization of the amount of transmitted light by infrared light;

FIG. 11 is a flowchart showing sequences of operations for data communication between the biometric information measuring apparatus and the personal computer;

DETAILED DESCRIPTION OF THE PREFERRED EMBODIMENTS OF THE INVENTION

Specific embodiments of the present invention are now described in detail with reference to the accompanying drawings, in which elements designated by like symbols have essentially the same configuration and a description of such elements will not be repeated.

First Embodiment

Figure 1:
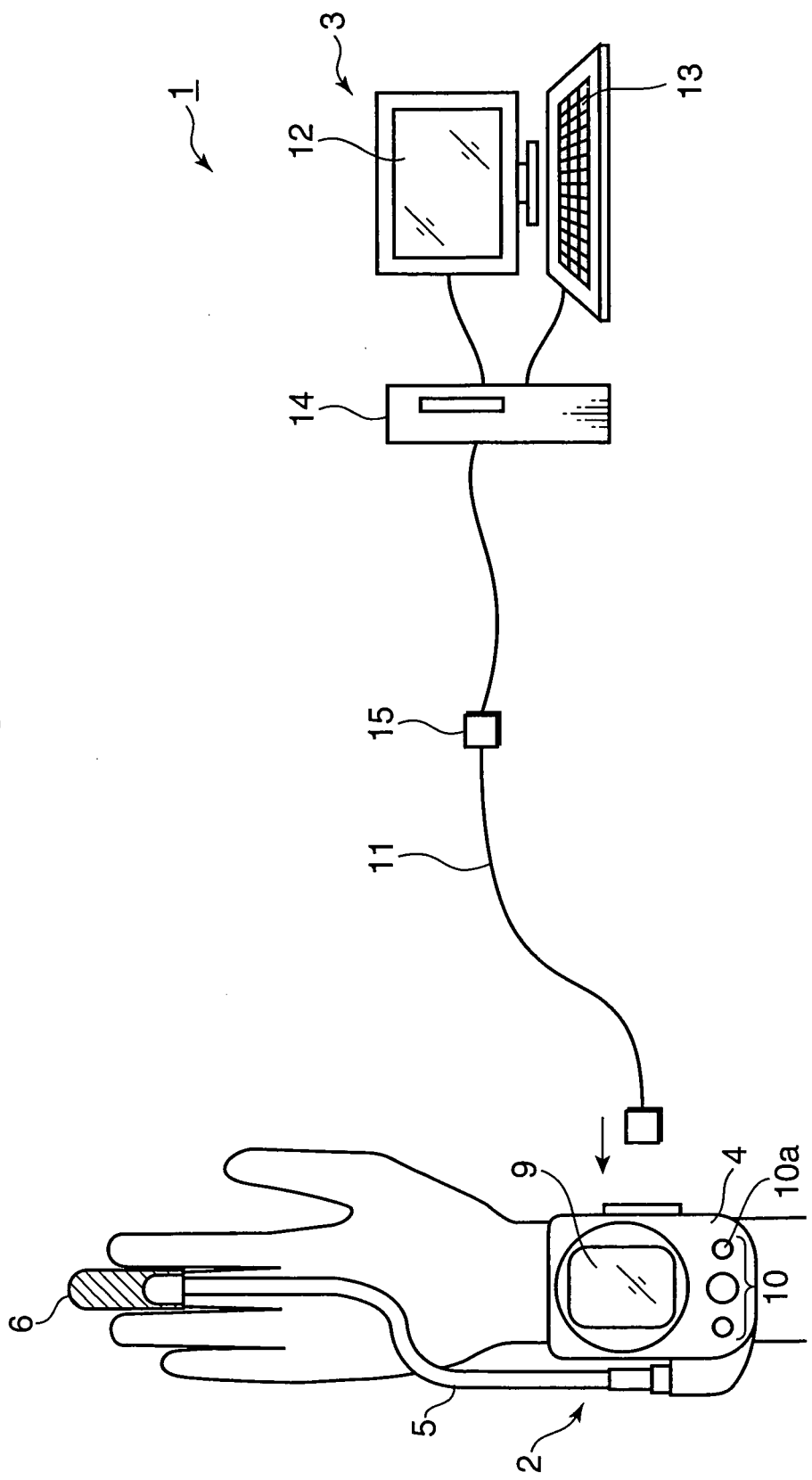
FIG. 1 is a diagram schematically showing the configuration of a biometric information measuring system according to a first embodiment of the invention.
Figure 2:
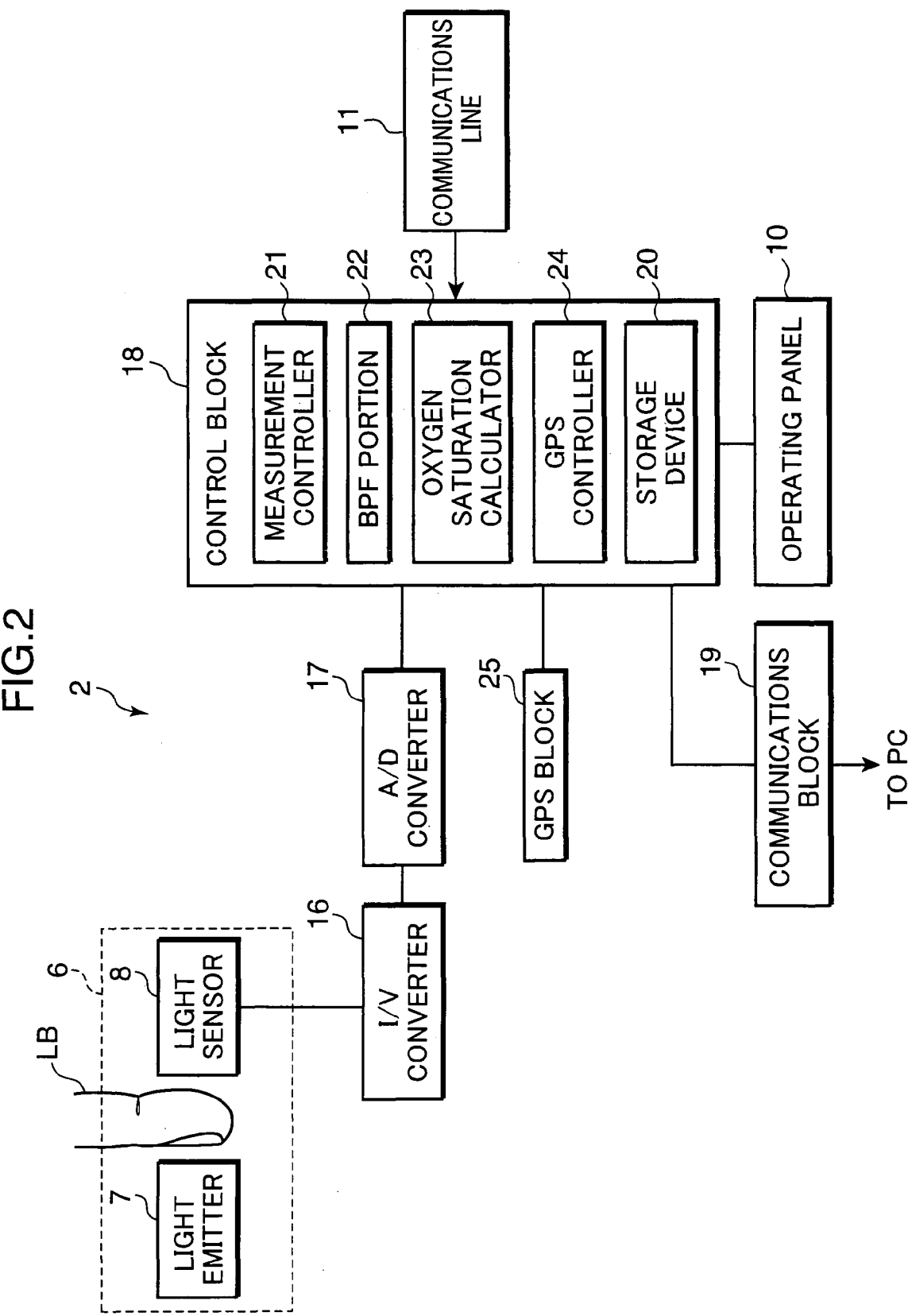
FIG. 2 is a block diagram showing the electrical configuration of a biometric information measuring apparatus of the biometric information measuring system of the first embodiment.

FIG. 1 is a diagram schematically showing the configuration of a biometric information measuring system 1 according to a first embodiment of the invention, and FIG. 2 is a block diagram showing the electrical configuration of a biometric information measuring apparatus 2 of the biometric information measuring system 1. The biometric information measuring system 1 includes the biometric information measuring apparatus 2 and a personal computer (PC) 3, for example, as shown in FIG. 1.

The biometric information measuring apparatus 2 of this embodiment is a portable pulse oximeter including a generally box-shaped main unit 4 and a fingerstall-like sensor unit 6 which is electrically connected to the main unit 4 by a cable 5, for example, as depicted in FIGS. 1 and 2. A subject can wear the main unit 4 on a wrist by means of a wrist strap (not shown) with the sensor unit 6 fitted on a fingertip for measurement.

The sensor unit 6 includes a light emitter 7 and a light sensor 8 which are disposed at specific relative positions to face each other. The light emitter 7 includes a light-emitting diode (LED) for emitting red light R with a wavelength $\lambda 1$ in a red light range and an LED for emitting infrared light IR with a wavelength $\lambda 2$ in an infrared light range. The light sensor 8 includes a photoelectric conversion device, such as a silicon photodiode which generates a current corresponding to a received light intensity. The light sensor 8 of this embodiment is sensitive at least to light components having the two wavelengths $\lambda 1$, $\lambda 2$. The light sensor 8 receives the light components of the two wavelengths $\lambda 1$, $\lambda 2$ which are emitted by light emitter 7 and pass through a living body tissue LB of the subject.

When fitted on the fingertip of the subject, the sensor unit 6 is disposed in such a fashion that the fingertip is sandwiched between the light emitter 7 and the light sensor 8. During a measurement, the light emitter 7 alternately emits the red light R of the wavelength $\lambda 1$ and the infrared light IR of the wavelength $\lambda 2$ and the light sensor 8 performs light-sensing operation in synchronism with light-emitting operation of the light emitter 7. A later-described control block 18 controls the light-emitting operation of the light emitter 7 and the light-sensing operation of the light sensor 8 in such a way that the sensor unit 6 emits and senses each of the red light R and the infrared light IR at specific intervals between $\frac{1}{40}$ to $\frac{1}{30}$ seconds. Upon receiving the red or infrared light, the light sensor 8 outputs a current signal of which value corresponds to the received light intensity to a later-described current-to-voltage (I/V) converter 16 provided in the main unit 4.

The main unit 4 has a display window 9 and an operating panel 10 provided adjacent to the display window 9. The main unit 4 operates on power fed from such a power source as a battery or a dry cell installed in an unillustrated battery chamber.

The display window 9 is made of such a display device as a liquid crystal display (LCD), a 7-segment light emitting diode (LED), an organic photoluminescence display, a cathode ray tube (CRT) display or a plasma display panel (PDP), for example, to display information including oxygen saturation data calculated by the control block 18 (refer to FIG. 2).

The operating panel 10 includes a power on/off button for turning on and off the main unit 4, a start button for entering an instruction for starting an oxygen saturation measurement and a stop button for entering an instruction for stopping the oxygen saturation measurement. When the start button is pressed, a later-described GPS block 25 determines the current location of the biometric information measuring apparatus 2 (or the subject) in terms of latitude and longitude and a later-described storage device 20 stores information on the current location.

The PC 3 includes a display unit 12, an operating terminal 13 and a main unit 14. The display unit 12 is made of such a display device as a CRT display, an LCD, A PDP display or a rear projection display, for example, to display data sent from the biometric information measuring apparatus 2 and various other pieces of information. The operating terminal 13 includes a keyboard and a mouse, for example, through which an operator can enter instructions and various pieces of information to cause a later-described control block 28 (refer to FIG. 8) to perform desired operations and processing tasks. The main unit 14 is provided with a communications block 26 and an external storage device 27, such as a hard disk, for storing various programs and data in addition to the aforementioned control block 28.

In the case where the biometric information measuring apparatus 2 of the biometric information measuring system 1 of the present embodiment is connected to the PC 3 by a communications line 11 with an isolator 15 inserted therein as illustrated in FIG. 2 so that the biometric information measuring apparatus 2 and the PC 3 can communicate with each other, the oxygen saturation data and other data acquired by the biometric information measuring apparatus 2 are sent to the PC 3, and the PC 3 displays these data and results of analysis thereof on the display unit 12. The isolator 15 is an optical isolator including a photocoupler, for instance, in which an electrical signal is converted into an optical signal which is reconverted into an electrical signal.

Referring again to FIG. 2, the biometric information measuring apparatus 2 includes an analog-to-digital (A/D) converter 17 and a communications block 19 in addition to the sensor unit 6, the display window 9, the operating panel 10, the I/V converter 16, the control block 18 and the GPS block 25 already mentioned.

The I/V converter 16 converts the aforementioned current signal output from the light sensor 8 at intervals of 1/40 seconds, for instance, into a voltage signal which is sent as a photoplethysmographic signal to the A/D converter 17. The A/D converter 17 converts the photoplethysmographic signal fed from the I/V converter 16 from an analog form into a digital form and delivers the digital photoplethysmographic signal to the control block 18.

The GPS block 25 is an example of a positioning device which determines the current location of the biometric information measuring apparatus 2 in terms of latitude and longitude by using radio waves transmitted from a plurality of artificial satellites.

The control block 18 which is configured with a microprocessor, a digital signal processor (DSP) and peripheral circuits, for example, calculates oxygen saturation of arterial blood from the input photoplethysmographic signal by using data and a program stored in the storage device 20. Specifically, the control block 18 includes such functional units as a measurement controller 21, a bandpass filter (BPF) portion 22, an oxygen saturation calculator 23, a GPS controller 24 and the aforementioned storage device 20.

The measurement controller 21 controls the light-emitting operation of the light emitter 7 and the light-sensing operation of the light sensor 8 of the sensor unit 6. In this embodiment, the measurement controller 21 controls the light emitter 7 to alternately emit the red light R of the wavelength $\lambda 1$ and the infrared light IR of the wavelength $\lambda 2$ so that the red light R and the infrared light IR are each emitted at the intervals of 1/40 seconds, for instance.

The BPF portion 22 is made of a digital filter for filtering the A/D-converted photoplethysmographic signal fed from the A/D converter 17. Alternatively, the BPF portion 22 may be made of a combination a digital low-pass filter and a digital high-pass filter or of a finite impulse response (FIR) filter.

The oxygen saturation calculator 23 calculates the oxygen saturation at each measuring point in time based on the photoplethysmographic signal filtered by the BPF portion 22. Now, a principle of blood oxygen saturation calculation by the oxygen saturation calculator 23 using optical information is explained below.

Hemoglobin (Hb) in the blood carries oxygen to individual body cells. Hemoglobin combines with oxygen in the lungs, forming oxyhemoglobin ($HbO_2$) therein. When deprived of oxygen in the living body cells, oxyhemoglobin returns to hemoglobin (i.e., deoxyhemoglobin in reduced form). The blood oxygen saturation ($SpO_2$) is the ratio of the amount of oxyhemoglobin in the blood. Expressing the concentration of hemoglobin in the blood by CHb and the concentration of oxyhemoglobin by $CHbO_2$, the blood oxygen saturation ($SpO_2$) is given by equation (1) below:

$$SPO_2(\%) = \frac{CHbO_2}{CHb + CHbO_2} \times 100 \qquad (1)$$

Figure 3:
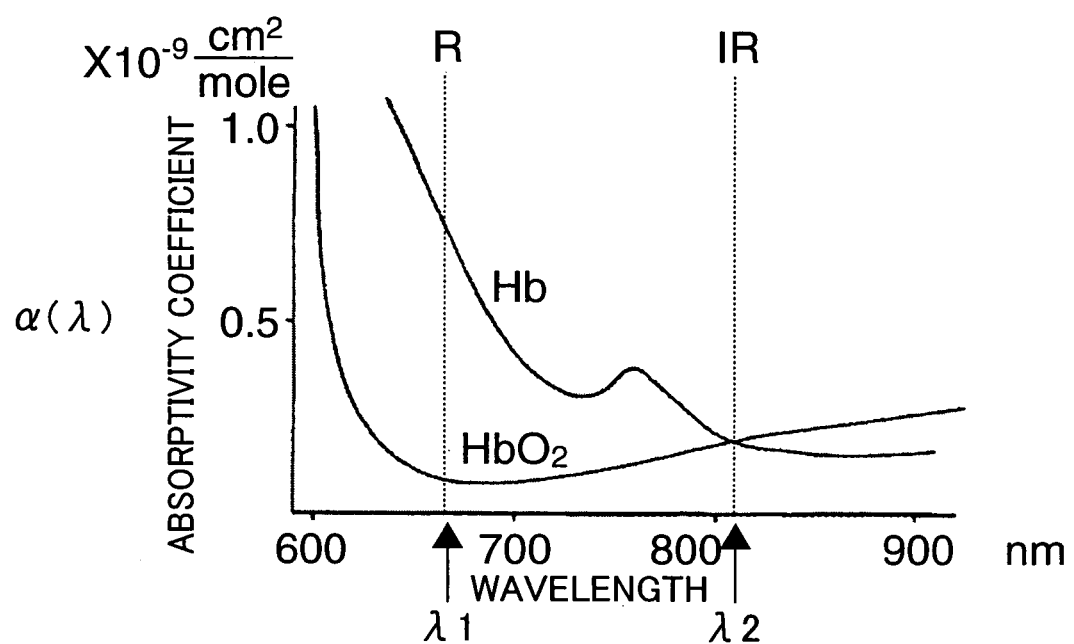
FIG. 3 is a graph showing light absorption characteristics of hemoglobin and oxyhemoglobin.

FIG. 3 is a graph showing light absorption characteristics of hemoglobin and oxyhemoglobin, in which a horizontal axis represents wavelength of light in nm and a vertical axis represents absorptivity coefficient in $10^{-9}$ cm$^2$/mole. On the other hand, absorbances of hemoglobin and oxyhemoglobin have dependence on wavelength so that absorptivity coefficients $\alpha(\lambda)$ of both exhibit the light absorption characteristics shown in FIG. 3.

As can be seen from FIG. 3, hemoglobin and oxyhemoglobin exhibit different light absorption characteristics. While hemoglobin absorbs a larger amount of light in a red light range including the red light R of the wavelength $\lambda 1$ than oxyhemoglobin, hemoglobin absorbs a smaller amount of light in an infrared light range at wavelengths of $\lambda 2$ and above including the infrared light IR of the wavelength $\lambda 2$ than oxyhemoglobin. Thus, if the wavelength $\lambda 1$ of the red light R is 660 nm at which a difference between the absorptivity coefficients of hemoglobin and oxyhemoglobin is at a maximum and the wavelength $\lambda 2$ of the infrared light IR is 815 nm at which the absorptivity coefficients of hemoglobin and oxyhemoglobin are equal to each other, for example, the amount of transmitted infrared light IR does not change even when the ratio between the concentrations of hemoglobin and oxyhemoglobin varies. On the other hand, the amount of transmitted red light R decreases with an increase in the concentration of hemoglobin, while the amount of transmitted red light R increases with an increase in the concentration of oxyhemoglobin. This means that it is possible to determine the blood oxygen saturation from the ratio between the amounts of transmitted red light R and infrared light IR.

The biometric information measuring apparatus 2 of the embodiment is configured to determine the blood oxygen saturation based on the aforementioned difference in the light absorption characteristics between hemoglobin and oxyhemoglobin with respect to the red light R and the infrared light IR.

It is also possible to determine heart rate by utilizing the difference in the light absorption characteristics between hemoglobin and oxyhemoglobin with respect to the red light R and the infrared light IR.

Figure 4A:
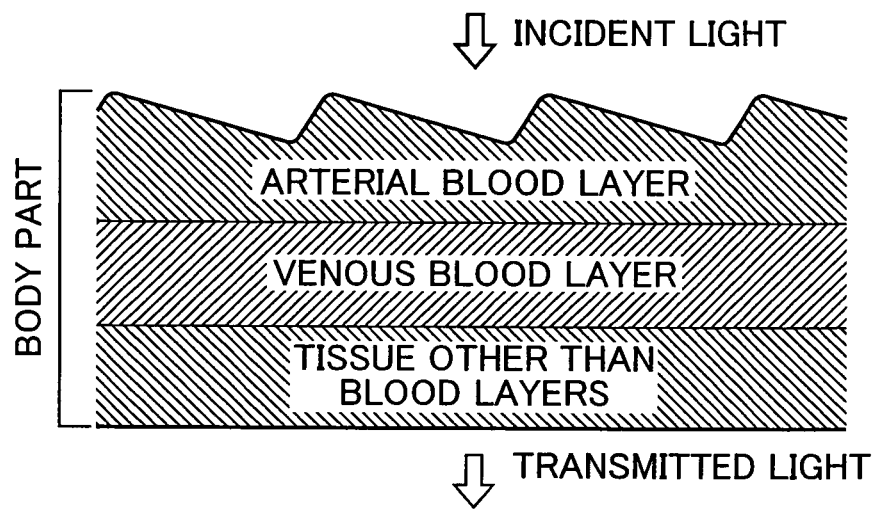
FIGS. 4A and 4B show how light is absorbed by a body part, FIG. 4A being a diagram showing the structure of a living body part and FIG. 4B being a diagram showing temporal variations in a photoplethysmographic signal.
Figure 4B:
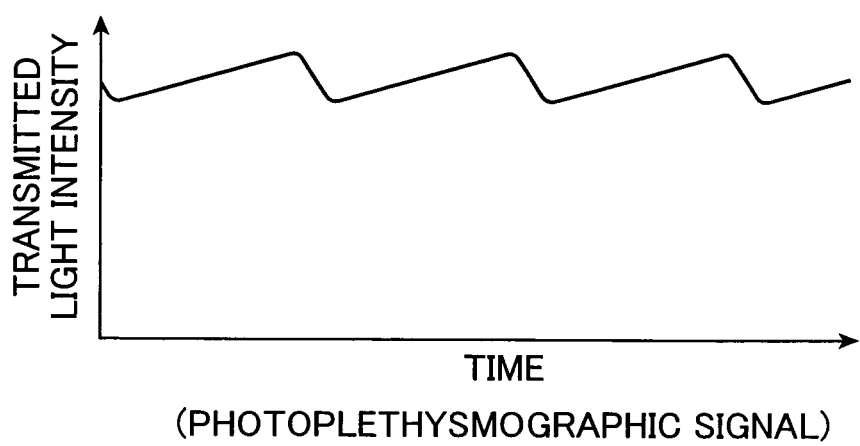
Figure 5A:
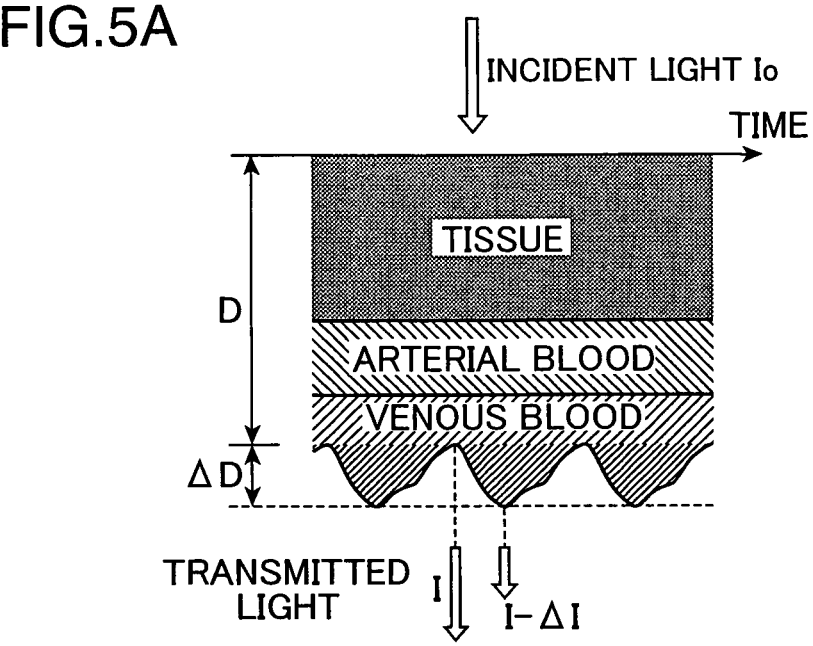
FIGS. 5A, 5B and 5C schematically show a relationship between incident light on a living body part and transmitted light, FIG. 5A being a diagram showing the relationship between the incident light and the transmitted light, FIG. 5B being an enlarged fragmentary diagram of FIG. 5A and FIG. 5C being a diagram showing temporal variations in the amount of the transmitted light.
Figure 5B:
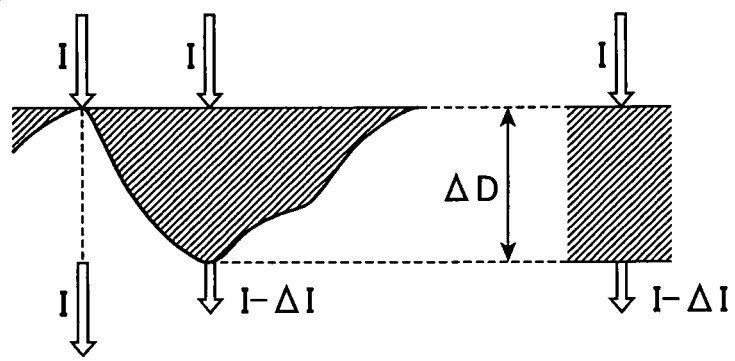
Figure 5C:
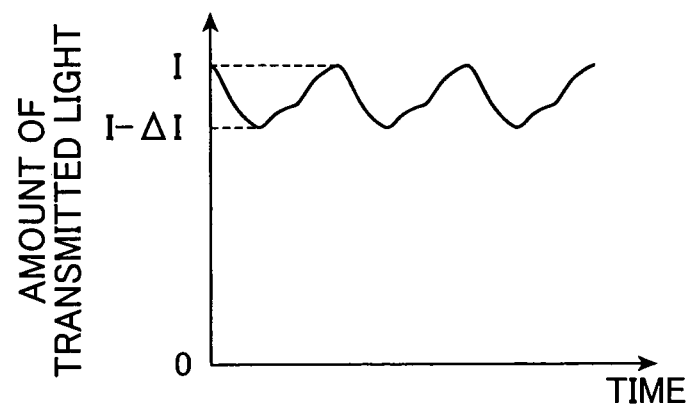
Figure 7:
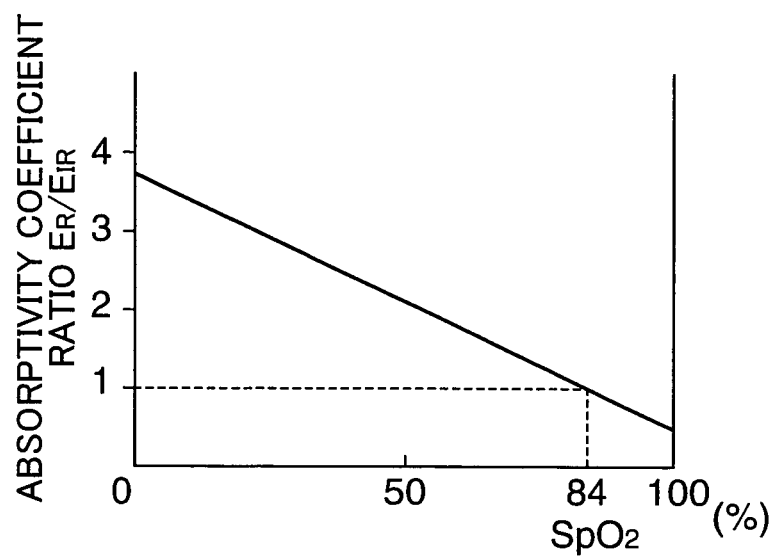
FIG. 7 is a graph showing a relationship between an absorptivity coefficient ratio and oxygen saturation.

FIGS. 4A and 4B are diagrams showing absorption of light by a living body part, in which a horizontal axis of FIG. 4B represents time and a vertical axis of FIG. 4B represents transmitted light intensity. FIGS. 5A, 5B and 5C are diagrams schematically showing a relationship between light incident on a living body part and light transmitted therethrough. FIG. 6 is a diagram for explaining normalization of the amount of transmitted light by infrared light, and FIG. 7 is a graph showing a relationship between the oxygen saturation $SpO_2$ (%) shown on a horizontal axis and ratio $E_R/E_{IR}$ of absorptivity coefficients for the red light R and the infrared light IR shown on a vertical axis.

When light is projected on a living body part, part of the incident light is absorbed by the body part while the remainder of the incident light propagates therethrough. Generally, the body part includes an arterial blood layer, a venous blood layer and a tissue other than the arterial and venous blood layers as shown in FIG. 4A. As can be seen from FIG. 4A, absorption of light by the body part occurs in the arterial blood layer, the venous blood layer and the tissue other than the arterial and venous blood layers. Since properties of the venous blood layer and the tissue other than the arterial and venous blood layers do not vary with the lapse of time, the amount of light absorption by the venous blood layer and the tissue other than the blood layers remains generally constant.

In contrast, properties of the arterial blood layer vary due to changes in diameter of blood vessels (arteries), so that the amount of light absorption by the arterial blood layer varies with heartbeats through the lapse of time as depicted in FIG. 4B. It can therefore be expected that variations in transmitted light intensity shown in FIG. 4B represent information on the arterial blood alone which is scarcely affected by the venous blood layer and the tissue other than the arterial and venous blood layers.

In order to compare variations in the amounts of transmitted red light R and infrared light IR, it is necessary to cancel out a difference in the amount of incident light.

It is practically difficult to equalize the amounts Io of red light R and infrared light IR incident on the living body part as shown in FIG. 5A. Even if the amounts Io of incident red light R and infrared light IR are equalized, it is impossible to compare variations in transmitted light intensity of the red light R and the infrared light IR caused by the arterial blood layer alone, because the venous blood layer and the tissue other than the blood layers have different extinction moduli for the red light R and the infrared light IR.

Here, a maximum amount of transmitted light produced when the arteries are most narrowed is expressed as I and a minimum amount of transmitted light produced when the arteries are most thickened is expressed as (I−ΔI). If light is projected in the amount I on the arterial blood layer of a thickness ΔD, the amount of light transmitted through the arterial blood layer is expected to equal (I−ΔI) as shown in FIGS. 5B and 5C.

The oxygen saturation calculator 23 normalizes the amount of transmitted light so that the amount $I_R$ of transmitted red light R and the amount $I_{IR}$ of transmitted infrared light IR coincide with each other ($I_{IR}'=I_R$) as shown in FIG. 6, whereby the oxygen saturation calculator 23 calculates the ratio $(\Delta I_R/I_R)/(\Delta I_{IR}/I_{IR})$ between variations in the amounts of red light R and infrared light IR transmitted through the arterial blood layer to determine the oxygen saturation.

A relationship between the amount of incident light and the amount of reflected light can be expressed by equation (2) below according to Lambert-Beer's law:

$$\log\left(\frac{I}{I-\Delta I}\right) = EC\Delta D \quad (2)$$

where E is the absorptivity coefficient of an absorbing medium and C is the concentration of the absorbing medium.

Substituting the wavelengths of the red light R and the infrared light IR in equation (2) above and taking ratios of the left and right sides thereof, equation (3) below is obtained:

$$\frac{\log\{I_R/(I_R-\Delta I_R)\}}{\log\{I_{IR}/(I_{IR}-\Delta I_{IR})\}} = \frac{E_R C \Delta D}{E_{IR} C \Delta D} = \frac{E_R}{E_{IR}} \quad (3)$$

where $I_R$ is the amount of transmitted red light R, $I_{IR}$ is the amount of transmitted infrared light IR, $E_R$ is the absorptivity coefficient of the arterial blood layer for the red light R and $E_{IR}$ is the absorptivity coefficient of the arterial blood layer for the infrared light IR.

The graph of FIG. 7 shows the relationship between the ratio $E_R/E_{IR}$ of the absorptivity coefficients of the arterial blood layer for the red light R and the infrared light IR and the oxygen saturation ($SpO_2$) when the wavelengths of the red light R and the infrared light IR are 660 nm and 815 nm, respectively, for example. It is seen from FIG. 7 that as the absorptivity coefficient ratio $E_R/E_{IR}$ decreases, the oxygen saturation ($SpO_2$) increases proportionally.

When the oxygen saturation calculator 23 calculates the oxygen saturation in the aforementioned manner, the storage device 20 stores data on the oxygen saturation. Also, when requested by the PC 3 to which the biometric information measuring apparatus 2 is communicatably connected, the control block 18 of the biometric information measuring apparatus 2 causes the communications block 19 to perform operation for transmitting data concerning biometric information (hereinafter referred to as the biometric information data) to the PC 3. Here, the biometric information data transmitted from the biometric information measuring apparatus 2 to the PC 3 may include not only the oxygen saturation data calculated by the oxygen saturation calculator 23 but also such data as R-R intervals determined from an electrocardiographic tracing and oxygen desaturation index (ODI) which are derived from the photoplethysmographic signal by conventionally known methods.

Returning to FIG. 2, the GPS controller 24 serves to control the working of the GPS block 25. In the biometric information measuring apparatus 2 of this embodiment, the GPS block 25 is caused to perform operation for acquiring information on the current location before execution of measuring operation by the sensor unit 6 when an instruction for starting an oxygen saturation measurement is entered by pressing the start button. When an instruction for stopping the oxygen saturation measurement is entered by pressing the stop button subsequently, the GPS block 25 terminates the oxygen saturation measurement.

The storage device 20 of the biometric information measuring apparatus 2 stores the oxygen saturation data calculated by the oxygen saturation calculator 23 in association with the current location determined by the GPS block 25. It is to be noted that information stored in the storage device 20 in association with the current location is not limited to the oxygen saturation data but may be the digital photoplethysmographic signal output from the A/D converter 17.

Figure 8:
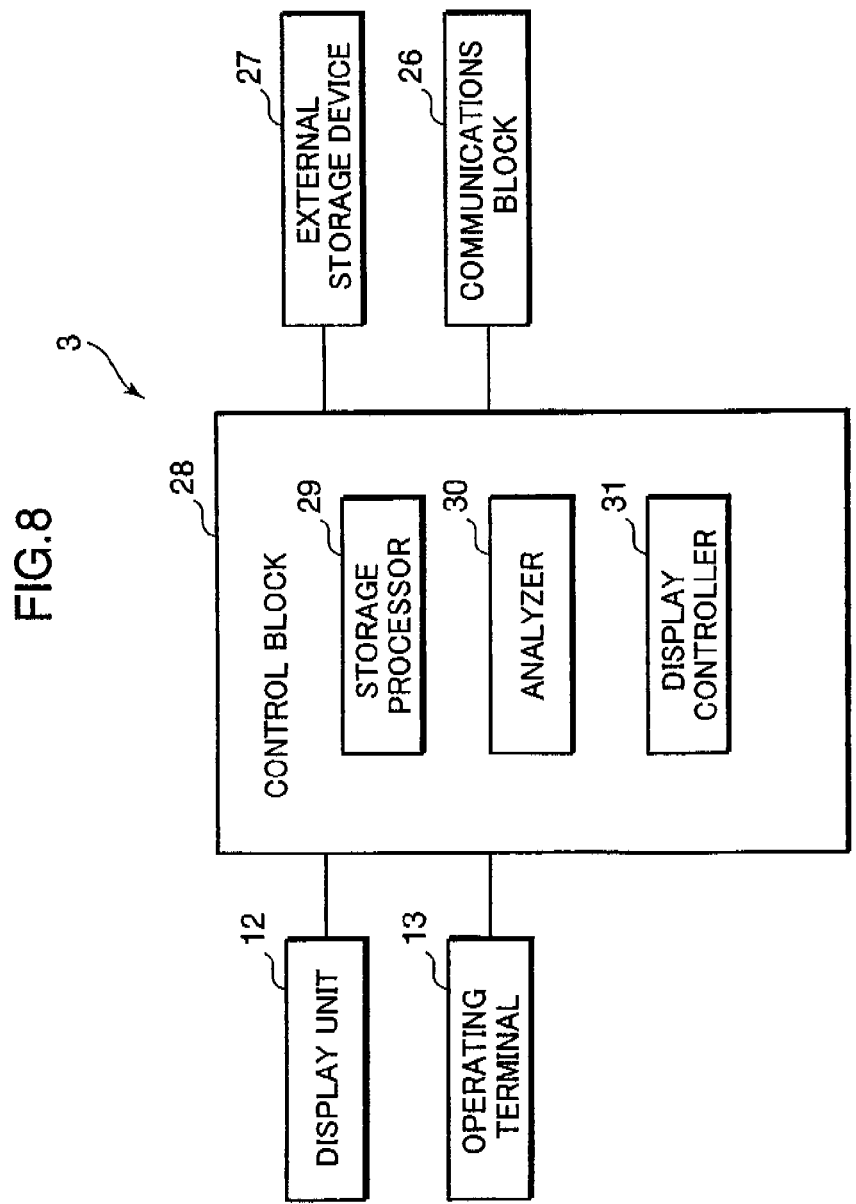
FIG. 8 is a block diagram showing the electrical configuration of a personal computer.

FIG. 8 is a block diagram showing the electrical configuration of the PC 3. The PC 3 includes the display unit 12, the operating terminal 13, the external storage device 27 and the control block 28 as already mentioned.

The communications block 26 employs a communications interface configured in conformity with such a standard as RS-232C, USB or IrDA, for example, to enable communication between the biometric information measuring apparatus 2 and the PC 3 through the communications line 11 and the isolator 15.

The external storage device 27 is configured with a hard disk, a USB memory, a compact disc (CD), a digital versatile disc (DVD) or a flexible disk, for example, to store data received through the communications block 26.

The control block 28 of the PC 3 is configured with a microcomputer, for example, for controlling operations of individual part of the PC 3 in an interrelated fashion. The control block 28 includes such functional units as a storage processor 29, an analyzer 30 and a display controller 31 as shown in FIG. 8.

The storage processor 29 controls the external storage device 27 so as to store the oxygen saturation data received from the biometric information measuring apparatus 2 through the communications block 26. The analyzer 30 analyzes the oxygen saturation data stored in the external storage device 27 to produce analysis values according to predefined content of analysis. The display controller 31 displays results of analysis obtained by the analyzer 30 on the display unit 12 in a specified form, such as a graph form.

Figure 9:
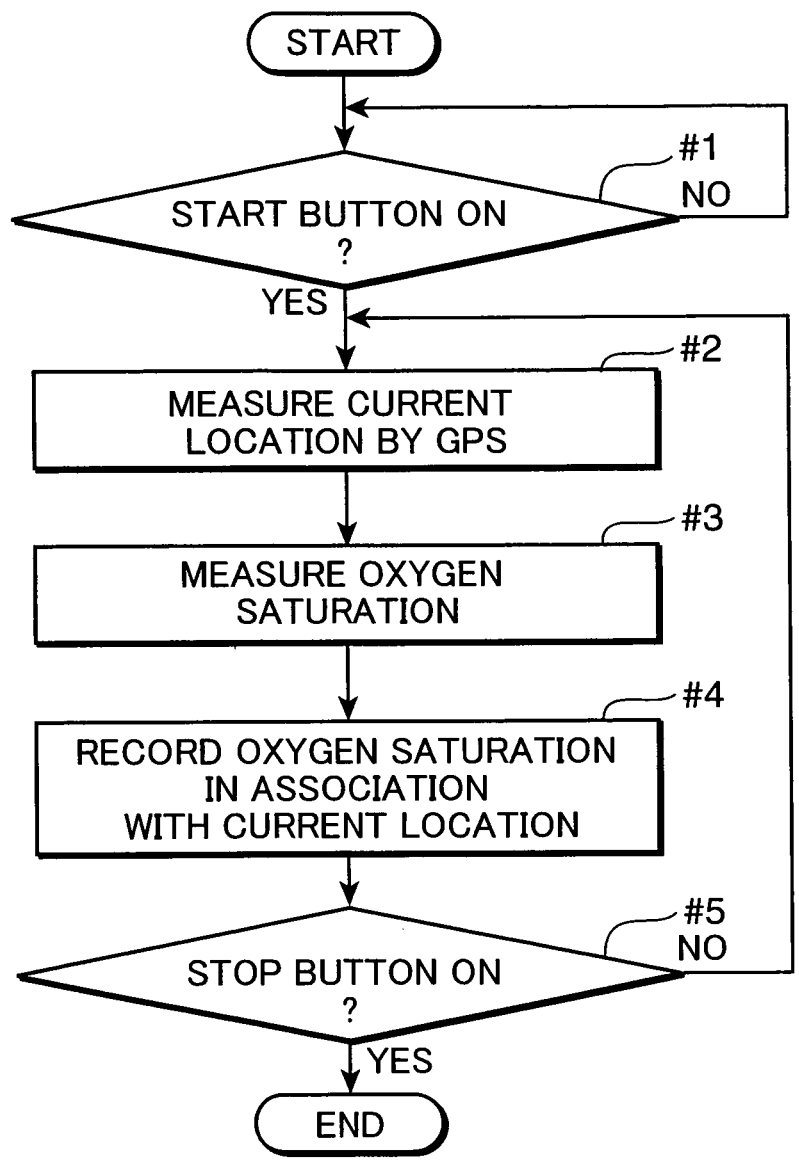
FIG. 9 is a flowchart showing a sequence of measuring operations performed by the biometric information measuring apparatus of the first embodiment of the invention.
Figure 10:
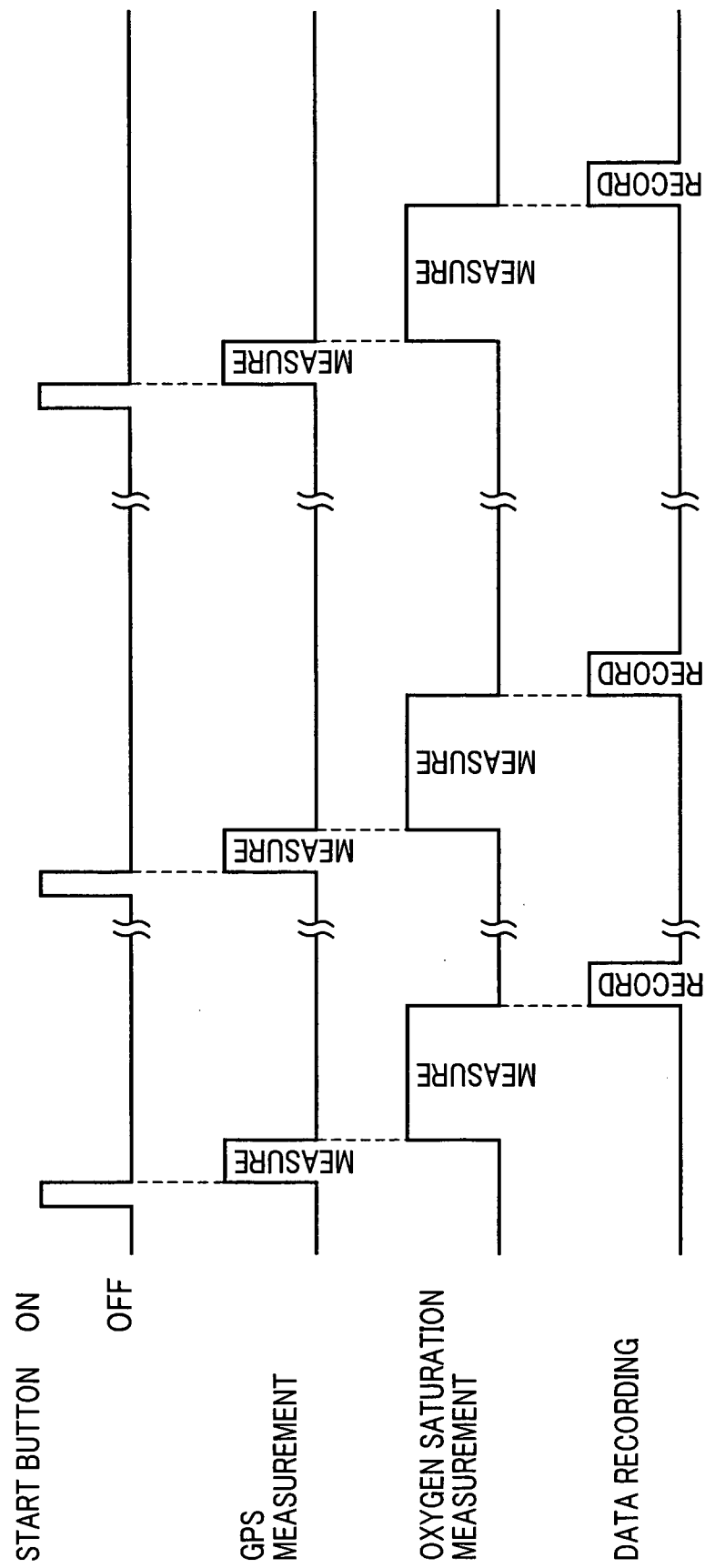
FIG. 10 is a time chart showing execution timing of the measuring operations performed by the biometric information measuring apparatus of the first embodiment of the invention.

Now, various operations and processing tasks performed by the biometric information measuring apparatus 2 and the PC 3 are described with reference to FIGS. 9 to 12. FIG. 9 is a flowchart showing a sequence of measuring operations performed by the biometric information measuring apparatus 2, and FIG. 10 is a time chart showing execution timing of the measuring operations, FIG. 10 including, from top to bottom, ON/OFF states of the start button, measuring cycles of the GPS block 25, oxygen saturation measuring cycles and data recording cycles.

When the subject presses the start button (Yes in step #1), the control block 18 causes the GPS block 25 to perform operation for measuring the current location in step #2. Then, the control block 18 causes the biometric information measuring apparatus 2 to perform operation for measuring the oxygen saturation in step #3 and store information on the measured oxygen saturation in association with information on the current location in the storage device 20 in step #4.

In succeeding step #5, the control block 18 judges whether the stop button has been pressed. If the stop button has not been pressed yet (No in step #5), the control block 18 returns to step #2. If the stop button has been pressed (Yes in step #5), on the other hand, the control block 18 terminates execution of the sequence of FIG. 9.

FIG. 11 is a flowchart showing sequences of operations for data communication between the biometric information measuring apparatus 2 and the PC 3 performed when the biometric information measuring apparatus 2 is communicatably connected to the PC 3. Shown at left in FIG. 11 is the sequence of operations followed by the biometric information measuring apparatus 2 and shown at right in FIG. 11 is the sequence of operations followed by the PC 3.

If the biometric information measuring apparatus 2 is communicatably connected to the PC 3 through the communications line 11 and the isolator 15, the biometric information measuring apparatus 2 and the PC 3 can carry out the sequences shown in FIG. 11. When the biometric information measuring apparatus 2 connected to the PC 3 through the communications line 11 and the isolator 15 is turned on, the biometric information measuring apparatus 2 becomes ready to start communication (Yes in step #11). Then, the control block 18 of the biometric information measuring apparatus 2 initializes the communications block 19 and other elements related to execution of data communication in step #12 and waits for a transmission request signal to be transmitted from the PC 3 requesting transmission of the oxygen saturation data in step #13.

On the other hand, when the PC 3 is powered on (Yes in step #21), the control block 28 of the PC 3 begins to wait for an operator input of an instruction requesting the biometric information measuring apparatus 2 to download the oxygen saturation data in step #22. When the operator enters the instruction for downloading (Yes in step #22), the control block 28 performs operation for transmitting the aforementioned transmission request signal to the biometric information measuring apparatus 2 in step #23. Then, the control block 28 waits for the oxygen saturation data to be received from the biometric information measuring apparatus 2 in step #24.

When the biometric information measuring apparatus 2 receives the transmission request signal from the PC 3 (Yes in step #13), the control block 18 performs operations for reading out the oxygen saturation data from the storage device 20 and transmitting the same to the PC 3 in step #14. Subsequently, the control block 18 repeatedly executes the operations of steps #13 through #15 until the biometric information measuring apparatus 2 is judged to have been powered off in step #15. When the biometric information measuring apparatus 2 is powered off (Yes in step #15), the control block 18 terminates execution of the sequence shown at left in FIG. 11.

When the PC 3 receives the oxygen saturation data from the biometric information measuring apparatus 2 (Yes in step #24), the control block 28 stores the oxygen saturation data in the external storage device 27 in step #25. In succeeding step #26, the control block 28 judges whether the operator has entered an instruction to terminate execution of the currently executed program. If the instruction to terminate execution of the program has not been entered (No in step #26), the control block 28 returns to step #22 and reexecutes the operations of steps #22 through #26. If the instruction to terminate execution of the program has been entered (Yes in step #26), the control block 28 terminates execution of the sequence shown at right in FIG. 11.

Figure 12:
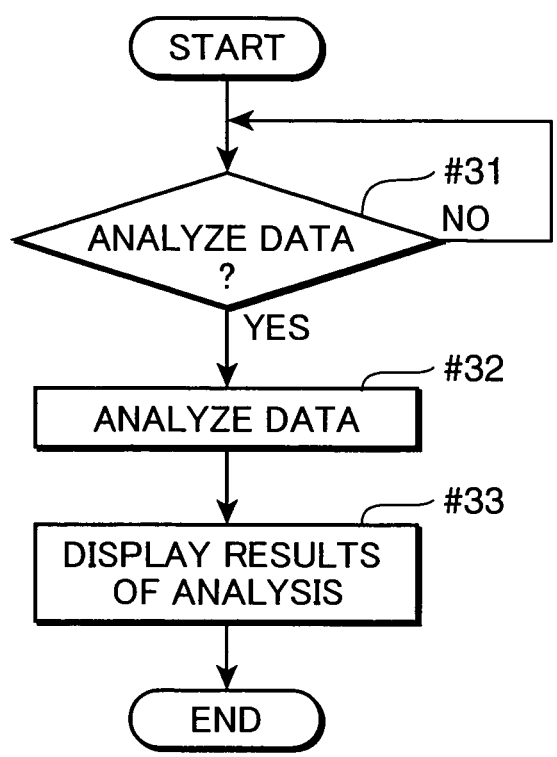
FIG. 12 is a flowchart showing a sequence of operations performed by the personal computer.

FIG. 12 is a flowchart showing a sequence of operations performed by the PC 3. When an instruction to analyze the oxygen saturation data according to predefined content of analysis is entered after the oxygen saturation data has been stored in the external storage device 27 (Yes in step #31), the control block 28 causes the analyzer 30 to analyze the oxygen saturation data in step #32 and causes the display controller 31 to display results of analysis on the display unit 12 in step #33.

As thus far described, the biometric information measuring apparatus 2 features a function to store the information on the current location of the sensor unit 6 in association with the information on the measured oxygen saturation, so that the biometric information measuring apparatus 2 can provide a medical expert (or the subject) with information on the state of the subject, such as his or her location, behavior and ambient conditions, at a point in time when the information on the oxygen saturation is acquired. Since the biometric information measuring apparatus 2 of the aforementioned embodiment makes it possible to know the location and behavior of the subject from the information on the current location at the time of measurement, the medical expert (or the subject) is allowed to conduct an analysis in a more proper manner.

The above-described arrangement of the first embodiment can be modified in various ways as discussed in the following with reference to second to sixth embodiments of the invention. The second to sixth embodiments differ from the first embodiment mainly in the working of the GPS block 25 so that the configurations shown in FIGS. 1 and 2 generally apply to the second to sixth embodiments as well. Accordingly, the following discussion of the second to sixth embodiments deals chiefly with differences from the first embodiment without repeating explanation of already discussed common aspects of these embodiments.

Second Embodiment

Figure 13:
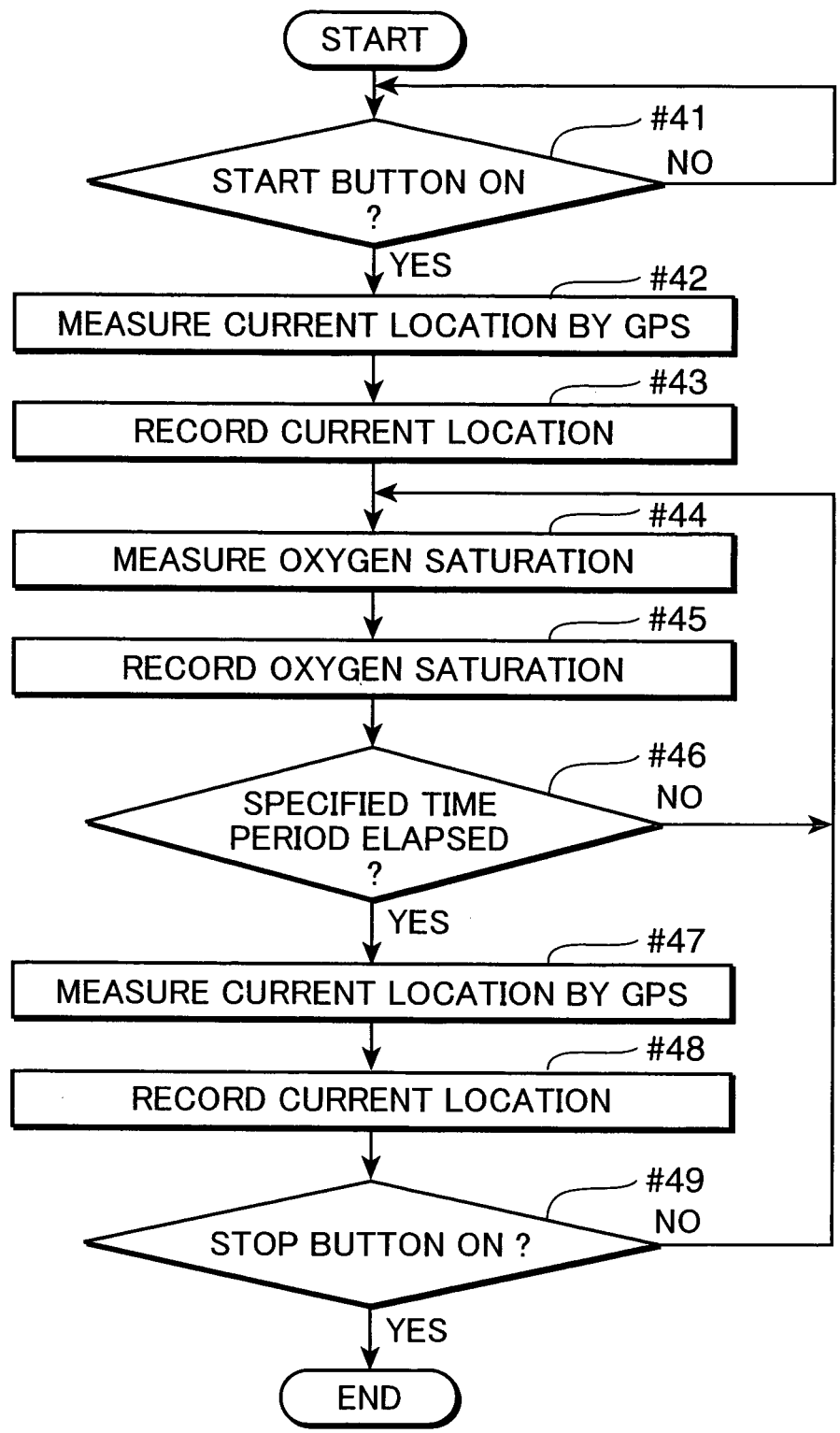
FIG. 13 is a flowchart showing a sequence of measuring operations performed by a biometric information measuring apparatus according to a second embodiment of the invention.
Figure 14:
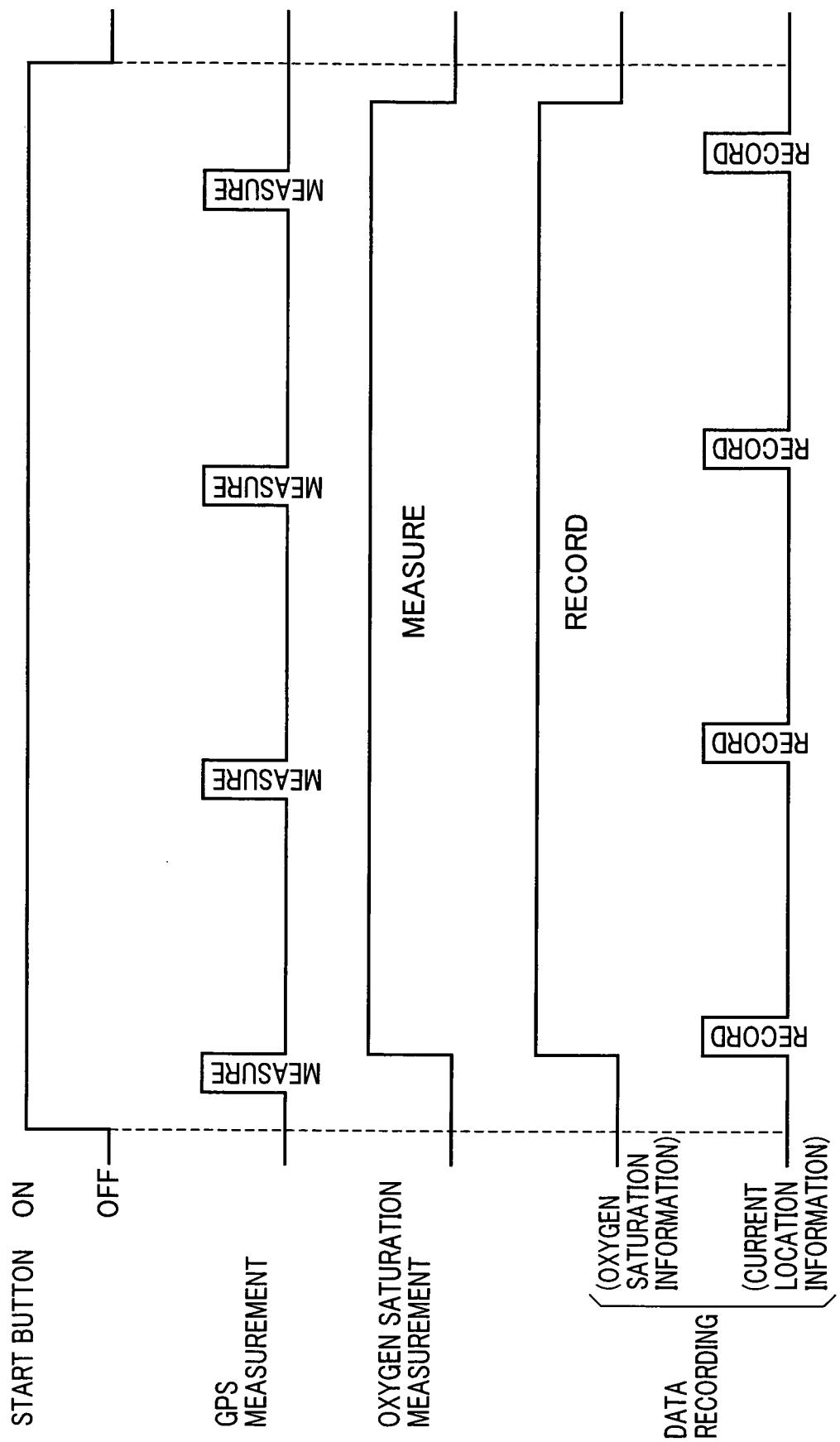
FIG. 14 is a time chart showing execution timing of the measuring operations performed by the biometric information measuring apparatus of the second embodiment of the invention.

A biometric information measuring apparatus 2 according to the second embodiment is configured to regularly measure and record the current location of the sensor unit 6 at specified time intervals during measurement of the oxygen saturation. FIG. 13 is a flowchart showing a sequence of measuring operations performed by the biometric information measuring apparatus 2 of the second embodiment, and FIG. 14 is a time chart showing execution timing of the measuring operations performed by the biometric information measuring apparatus 2 of the second embodiment, FIG. 14 including, from top to bottom, ON/OFF states of the start button, measuring cycles of the GPS block 25, oxygen saturation measuring cycles and data recording cycles.

When the subject presses the start button (Yes in step #41), the control block 18 causes the GPS block 25 to perform operation for measuring the current location in step #42. Then, the control block 18 causes the biometric information measuring apparatus 2 to store information on the current location in the storage device 20 in step #43 and measure the oxygen saturation in step #44.

Upon completion of the oxygen saturation measurement, the control block 18 causes the biometric information measuring apparatus 2 to store information on the oxygen saturation in the storage device 20 in step #45. At this point, the control block 18 causes the storage device 20 to store the information on the oxygen saturation in association with information on most recently measured one of previously obtained current locations. Proceeding to step #46, the control block 18 judges whether a specified period of time has elapsed from the latest measurement of the current location. If the control block 18 judges that the specified period of time has not elapsed yet (No in step #46), the control block 18 returns to step #44. If the control block 18 judges that the specified period of time has elapsed (Yes in step #46), the control block 18 causes the GPS block 25 to perform the operation for measuring the current location again in step #47 and causes the biometric information measuring apparatus 2 to store information on the current location in the storage device 20 in step #48. With this arrangement, the biometric information measuring apparatus 2 measures and records the current location of the sensor unit 6 at the specified time intervals while continually measuring and recording the oxygen saturation.

In succeeding step #49, the control block 18 judges whether the stop button has been pressed. If the stop button has not been pressed yet (No in step #49), the control block 18 returns to step #44. If the stop button has been pressed (Yes in step #49), on the other hand, the control block 18 terminates execution of the sequence of FIG. 13.

The biometric information measuring apparatus 2 of the above-described second embodiment can provide the medical expert, for instance, with detailed information on changes in the current location of the sensor unit 6 after each point in time when the information on the oxygen saturation is acquired, making it possible to analyze the oxygen saturation information in a more proper manner.

Third Embodiment

A biometric information measuring apparatus 2 according to the third embodiment is configured to measure the oxygen saturation only at a specified (preregistered) measuring cite. The biometric information measuring apparatus 2 of this embodiment has a current location registration button 10a on the operating panel 10 for entering an instruction for registering the current location (refer to FIG. 1). When the current location registration button 10a is pressed, the GPS block 25 determines the current location of the sensor unit 6 in terms of latitude and longitude and the biometric information measuring apparatus 2 registers this location as the measuring cite, whereby information on the oxygen saturation will be stored in association with information on the current location in the storage device 20 only when the current location matches the preregistered measuring cite.

Figure 15:
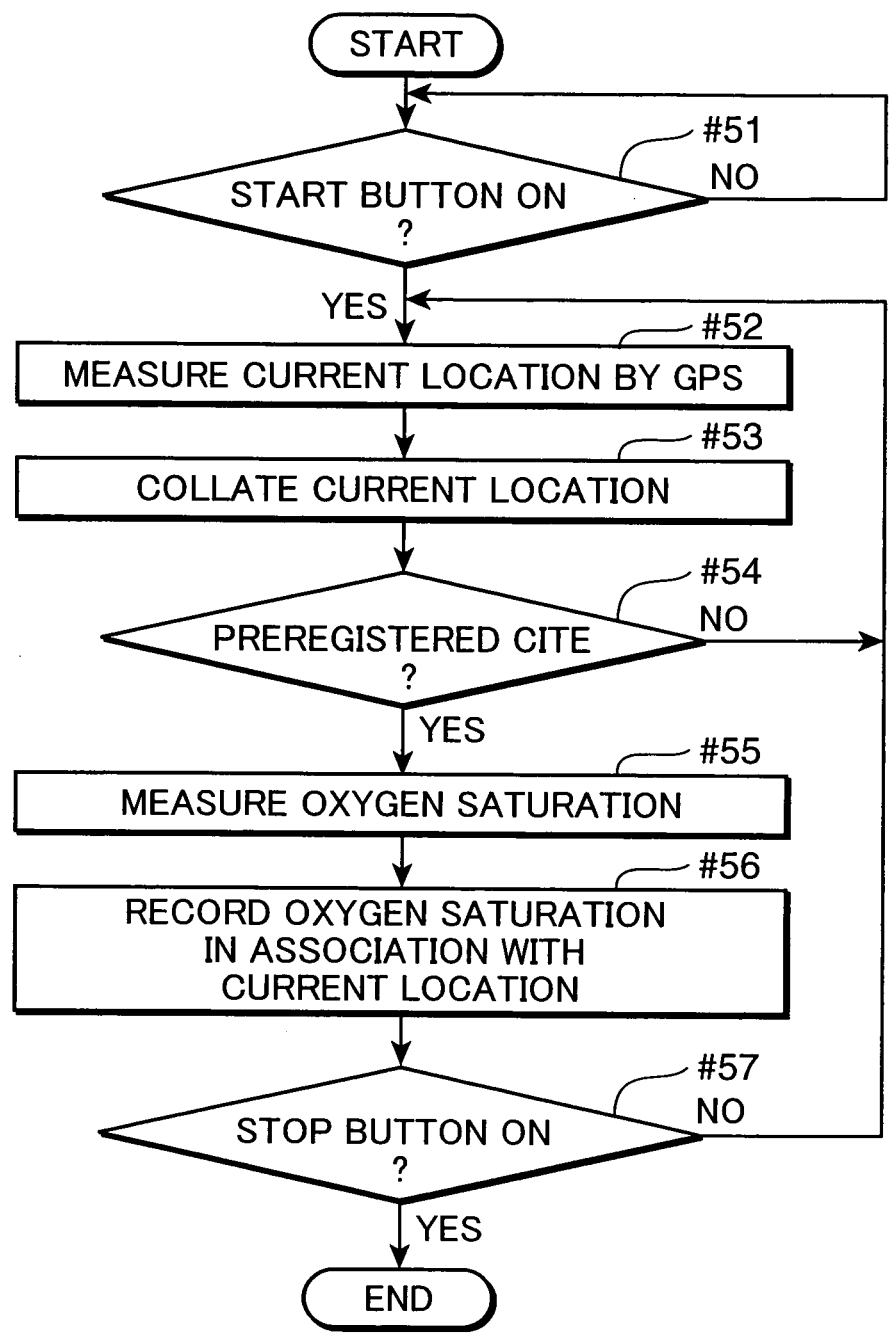
FIG. 15 is a flowchart showing a sequence of measuring operations performed by a biometric information measuring apparatus according to a third embodiment of the invention.
Figure 16:
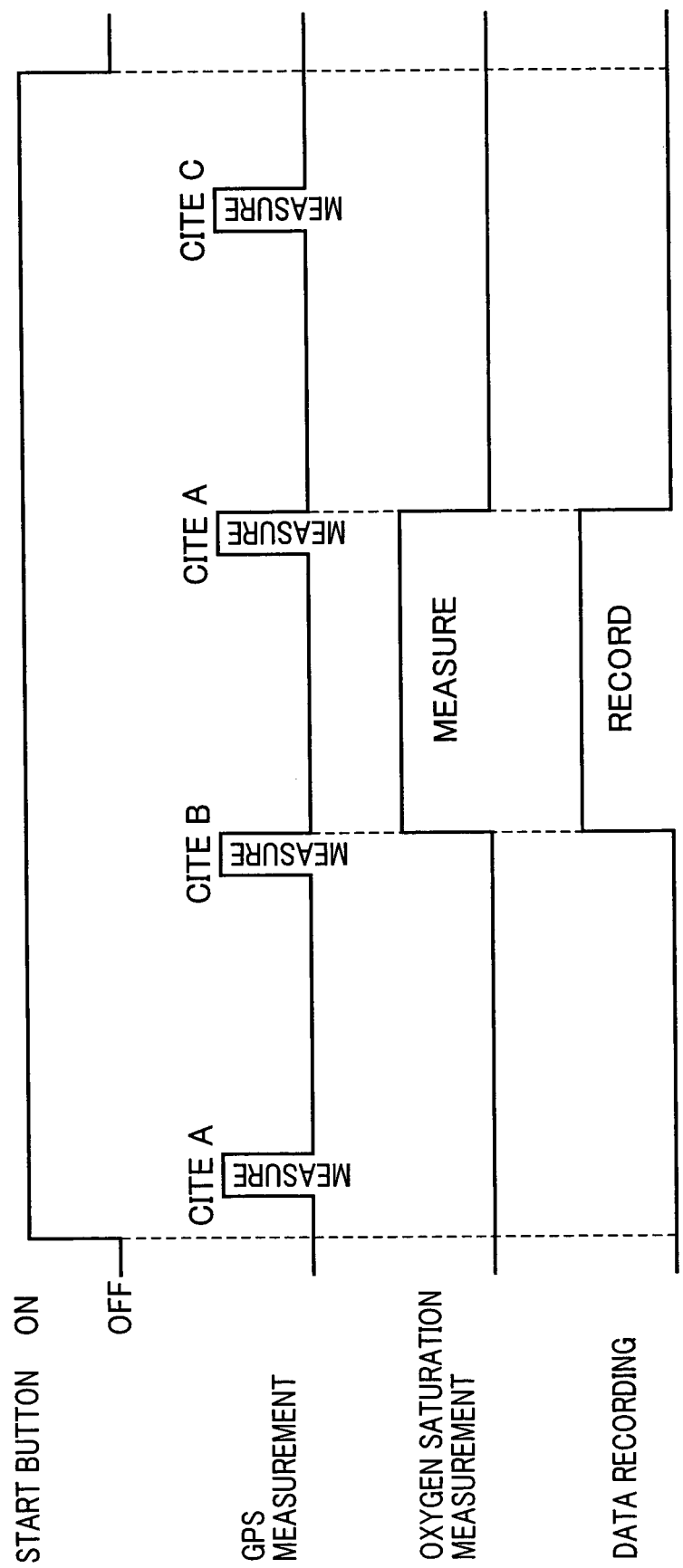
FIG. 16 is a time chart showing execution timing of the measuring operations performed by the biometric information measuring apparatus of the third embodiment of the invention.

FIG. 15 is a flowchart showing a sequence of measuring operations performed by the biometric information measuring apparatus 2 of the third embodiment, and FIG. 16 is a time chart showing execution timing of the measuring operations performed by the biometric information measuring apparatus 2 of the third embodiment, FIG. 16 including, from top to bottom, ON/OFF states of the start button, measuring cycles of the GPS block 25, oxygen saturation measuring cycles and data recording cycles. The following discussion of the sequence of FIG. 15 is based on the assumption that a specific measuring cite is already registered in the biometric information measuring apparatus 2.

When the subject presses the start button (Yes in step #51), the control block 18 causes the GPS block 25 to perform operation for measuring the current location in step #52. Then, the control block 18 collates the measured current location in step #53 and judges whether the current location matches the preregistered measuring cite in step #54.

If the current location is not judged to match the preregistered measuring cite (No in step #54), the control block 18 returns to step #52. If the current location is judged to match the preregistered measuring cite (Yes in step #54), on the other hand, the control block 18 causes the biometric information measuring apparatus 2 to measure the oxygen saturation in step #55 and store information on the measured oxygen saturation in association with information on the current location in the storage device 20 in step #56.

In succeeding step #57, the control block 18 judges whether the stop button has been pressed. If the stop button has not been pressed yet (No in step #57), the control block 18 returns to step #52. If the stop button has been pressed (Yes in step #57), on the other hand, the control block 18 terminates execution of the sequence of FIG. 15.

As depicted in the time chart of FIG. 16, "cite B" is the only measuring cite preregistered in the biometric information measuring apparatus 2, so that the biometric information measuring apparatus 2 measures the oxygen saturation and stores the information on the measured oxygen saturation in association with the information on the current location (cite B) in the storage device 20 only when the start button is pressed and the current location matches the preregistered measuring cite (cite B).

According to the third embodiment discussed above, the biometric information measuring apparatus 2 features a function that allows preregistration of the desired measuring cite, whereby the biometric information measuring apparatus 2 stores the information on the measured oxygen saturation in association with the information on the current location only when the current location determined by the GPS block 25 matches the preregistered measuring cite. Therefore, the biometric information measuring apparatus 2 of the third embodiment can provide the medical expert, for instance, with precise information on the oxygen saturation together with information on the location and behavior of the subject, making it possible to analyze the acquired oxygen saturation information in a more proper manner.

Fourth Embodiment

Figure 17:
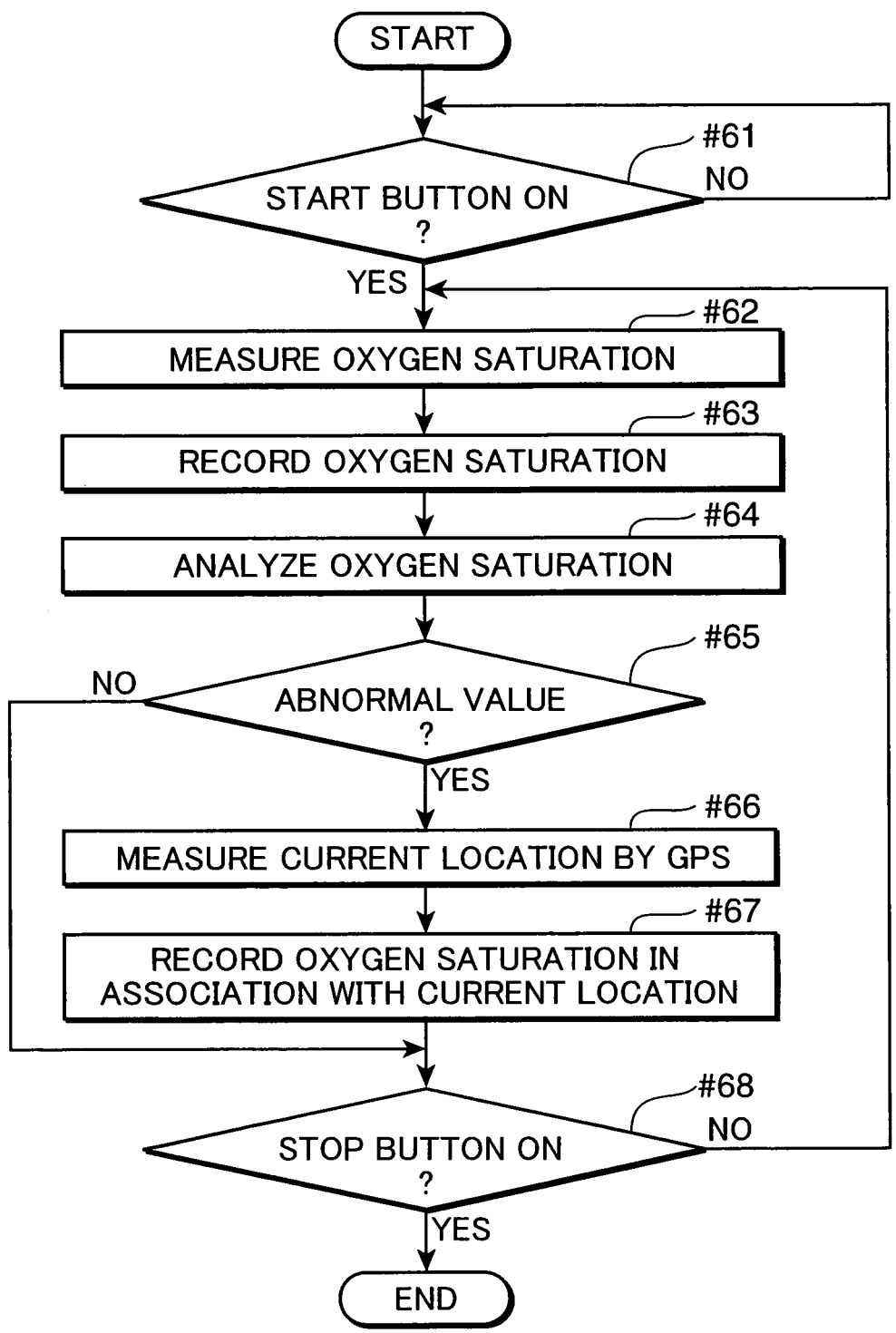
FIG. 17 is a flowchart showing a sequence of measuring operations performed by a biometric information measuring apparatus according to a fourth embodiment of the invention.

A biometric information measuring apparatus 2 according to the fourth embodiment is configured to record information on the oxygen saturation in association with information on the current location in the storage device 20 only when a measured oxygen saturation value is abnormal. FIG. 17 is a flowchart showing a sequence of measuring operations performed by the biometric information measuring apparatus 2 of the fourth embodiment.

When the subject presses the start button (Yes in step #61), the control block 18 causes the biometric information measuring apparatus 2 to measure the oxygen saturation in step #62 and store information on the oxygen saturation in the storage device 20 in step #63. Then, the control block 18 analyzes the oxygen saturation data stored in the storage device 20 according to a predefined analyzing routine in step #64.

In succeeding step #65, the control block 18 judges whether an oxygen saturation value obtained in step #64 is an abnormal value. If the oxygen saturation value is an abnormal value (Yes in step #65), the control block 18 causes the GPS block 25 to perform operation for measuring the current location in step #66 and the biometric information measuring apparatus 2 stores the oxygen saturation value in association with information on the current location in the storage device 20 in step #67. If the oxygen saturation value is not an abnormal value (No in step #65), on the other hand, the control block 18 skips steps #66 and #67 and proceeds to step #68.

In succeeding step #68, the control block 18 judges whether the stop button has been pressed. If the stop button has not been pressed yet (No in step #68), the control block 18 returns to step #62. If the stop button has been pressed (Yes in step #68), on the other hand, the control block 18 terminates execution of the sequence of FIG. 17.

According to the aforementioned arrangement of the fourth embodiment, the biometric information measuring apparatus 2 provides the medical expert, for instance, with information on conditions of the subject when an abnormal oxygen saturation value is detected. This makes it possible to analyze the acquired oxygen saturation in a more proper manner.

Fifth Embodiment

A biometric information measuring apparatus 2 according to the fifth embodiment is configured to provide capability to measure not only the oxygen saturation but also other kinds of biometric information and relate the individual kinds of biometric information to specific measuring cites. Specifically, the biometric information measuring apparatus 2 measures and records a particular kind of biometric information only when the subject is at a registered measuring cite to which the biometric information is related. The biometric information measuring apparatus 2 of the fifth embodiment, like that of the third embodiment, has a current location registration button 10a on the operating panel 10 for entering an instruction for registering the current location (refer to FIG. 1). When one kind of biometric information is selected and the current location registration button 10a is pressed, the GPS block 25 determines the current location of the biometric information measuring apparatus 2 in terms of latitude and longitude and the biometric information measuring apparatus 2 registers this location as the measuring cite of the selected kind of biometric information. For the sake of explanation, the following discussion of the embodiment adopts an example in which the biometric information measuring apparatus 2 can measure biometric information A and biometric information B which are related to preregistered measuring cites A and B, respectively. The measuring cites A and B may be a bathroom, a bedroom, a toilet or a living room in a private residence of the subject, or a toilet or a waiting space in a hospital, for example.

Figure 18:
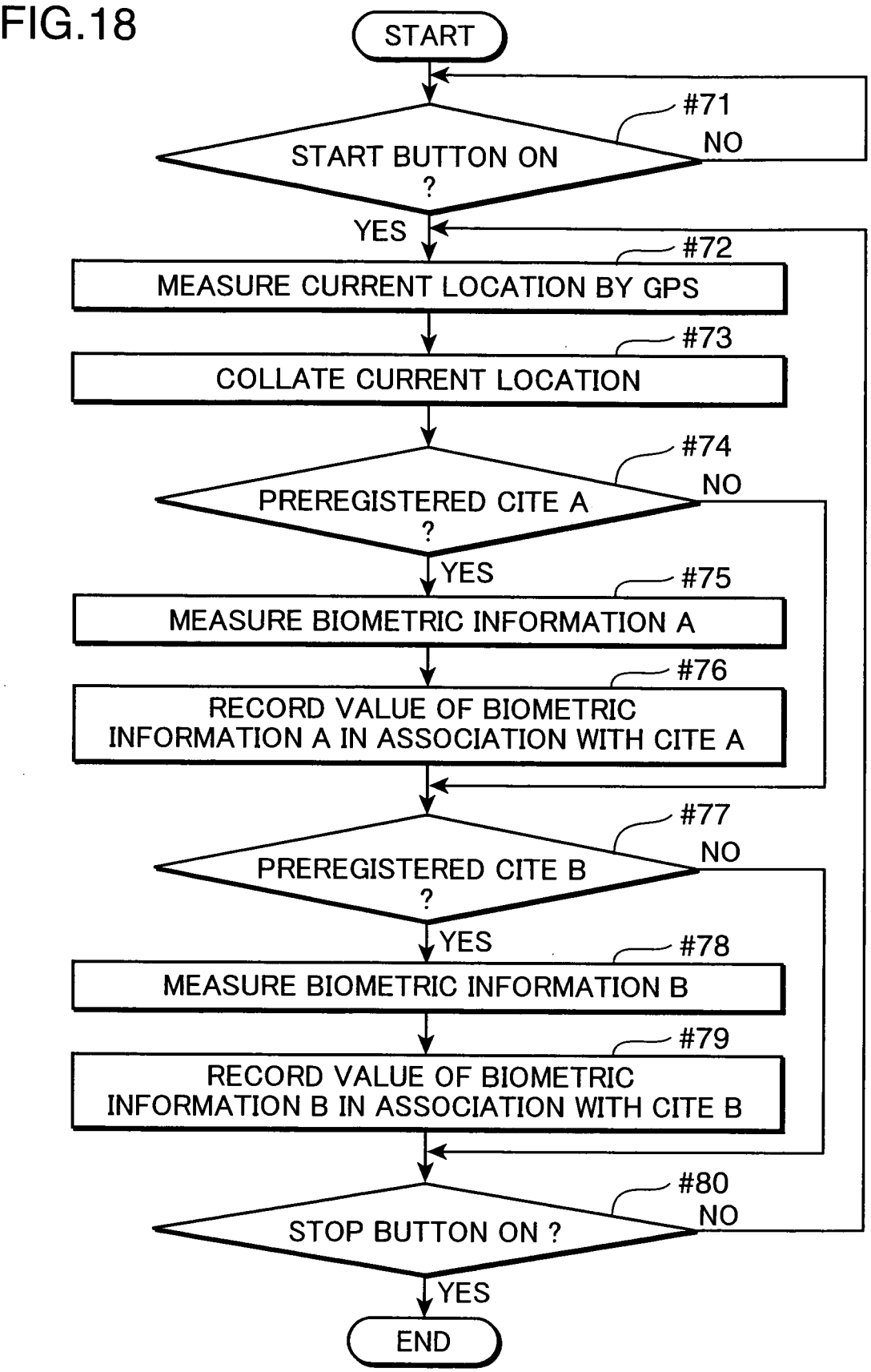
FIG. 18 is a flowchart showing a sequence of measuring operations performed by a biometric information measuring apparatus according to a fifth embodiment of the invention.
Figure 19:
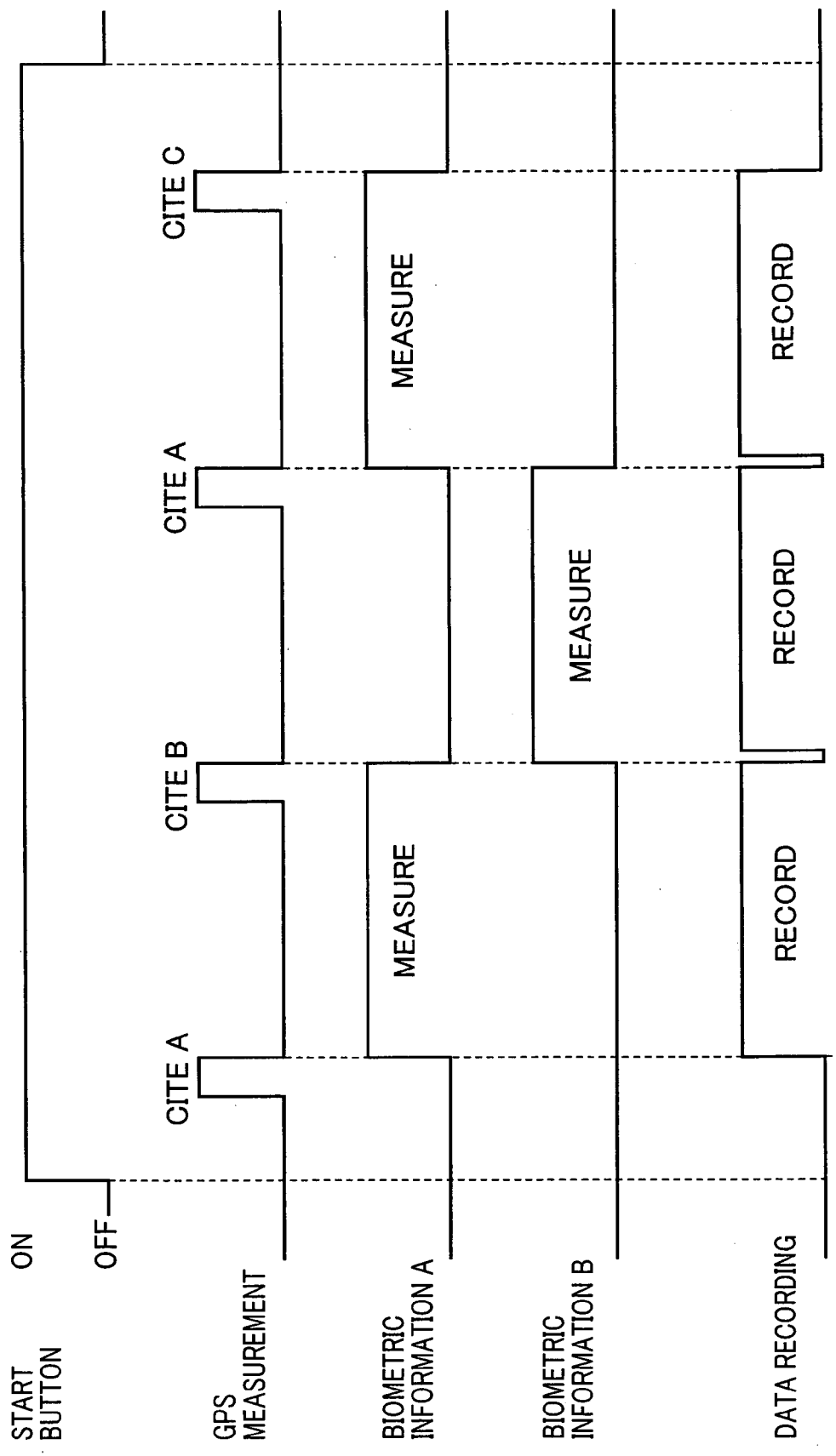
FIG. 19 is a time chart showing execution timing of the measuring operations performed by the biometric information measuring apparatus of the fifth embodiment of the invention.

FIG. 18 is a flowchart showing a sequence of measuring operations performed by the biometric information measuring apparatus 2 of the fifth embodiment, and FIG. 19 is a time chart showing execution timing of the measuring operations performed by the biometric information measuring apparatus 2 of the fifth embodiment, FIG. 19 including, from top to bottom, ON/OFF states of the start button, measuring cycles of the GPS block 25, measuring cycles of the biometric information A, measuring cycles of the biometric information B and data recording cycles.

When the subject presses the start button (Yes in step #71), the control block 18 causes the GPS block 25 to perform operation for measuring the current location in step #72. Then, the control block 18 collates the measured current location in step #73.

In succeeding step #74, the control block 18 judges whether the measured current location matches the preregistered measuring cite A. If the current location is judged to match the preregistered measuring cite A (Yes in step #74), the control block 18 causes the biometric information measuring apparatus 2 to measure the biometric information A in step #75 and store a measurement value of the biometric information A in association with information on the measuring cite A in the storage device 20 in step #76.

If the current location is not judged to match the preregistered measuring cite A (No in step #74), on the other hand, the control block 18 skips steps #75 and #76 and proceeds to step #77 to judge whether the measured current location matches the preregistered measuring cite B. If the current location is judged to match the preregistered measuring cite B (Yes in step #77), the control block 18 causes the biometric information measuring apparatus 2 to measure the biometric information B in step #78 and store a measurement value of the biometric information B in association with information on the measuring cite B in the storage device 20 in step #79.

If the current location is not judged to match the preregistered measuring cite B (No in step #77), on the other hand, the control block 18 skips steps #78 and #79 and proceeds to step #80.

In succeeding step #80, the control block 18 judges whether the stop button has been pressed. If the stop button has not been pressed yet (No in step #80), the control block 18 returns to step #72. If the stop button has been pressed (Yes in step #80), on the other hand, the control block 18 terminates execution of the sequence of FIG. 18.

The biometric information measuring apparatus 2 of the above-described fifth embodiment can provide the medical expert, for instance, with biometric information appropriately chosen for each measuring cite, making it possible to properly analyze different kinds of biometric information acquired at specified measuring cites.

Sixth Embodiment

Figure 20:
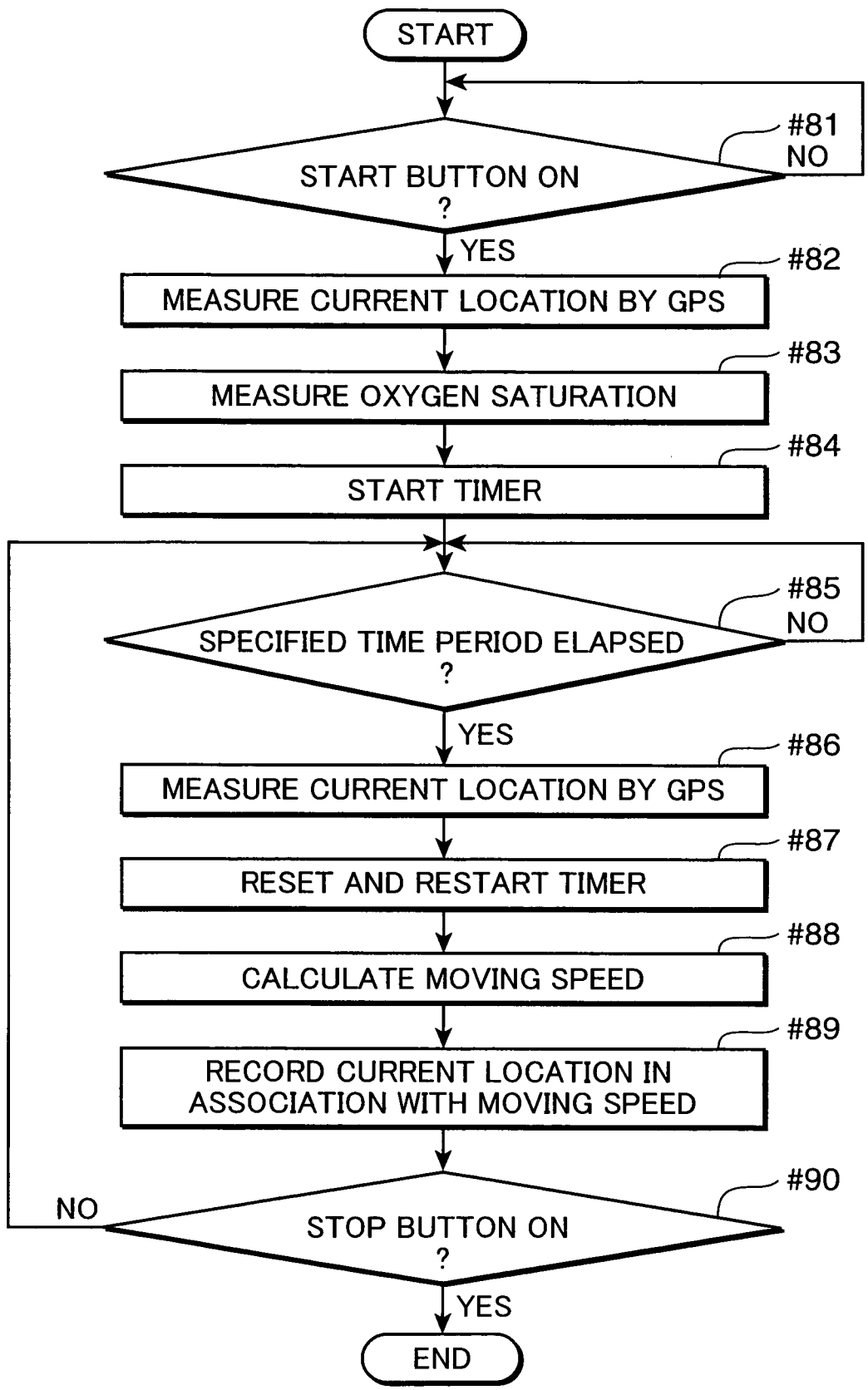
FIG. 20 is a flowchart showing a sequence of measuring operations performed by a biometric information measuring apparatus according to a sixth embodiment of the invention.
Figure 21:
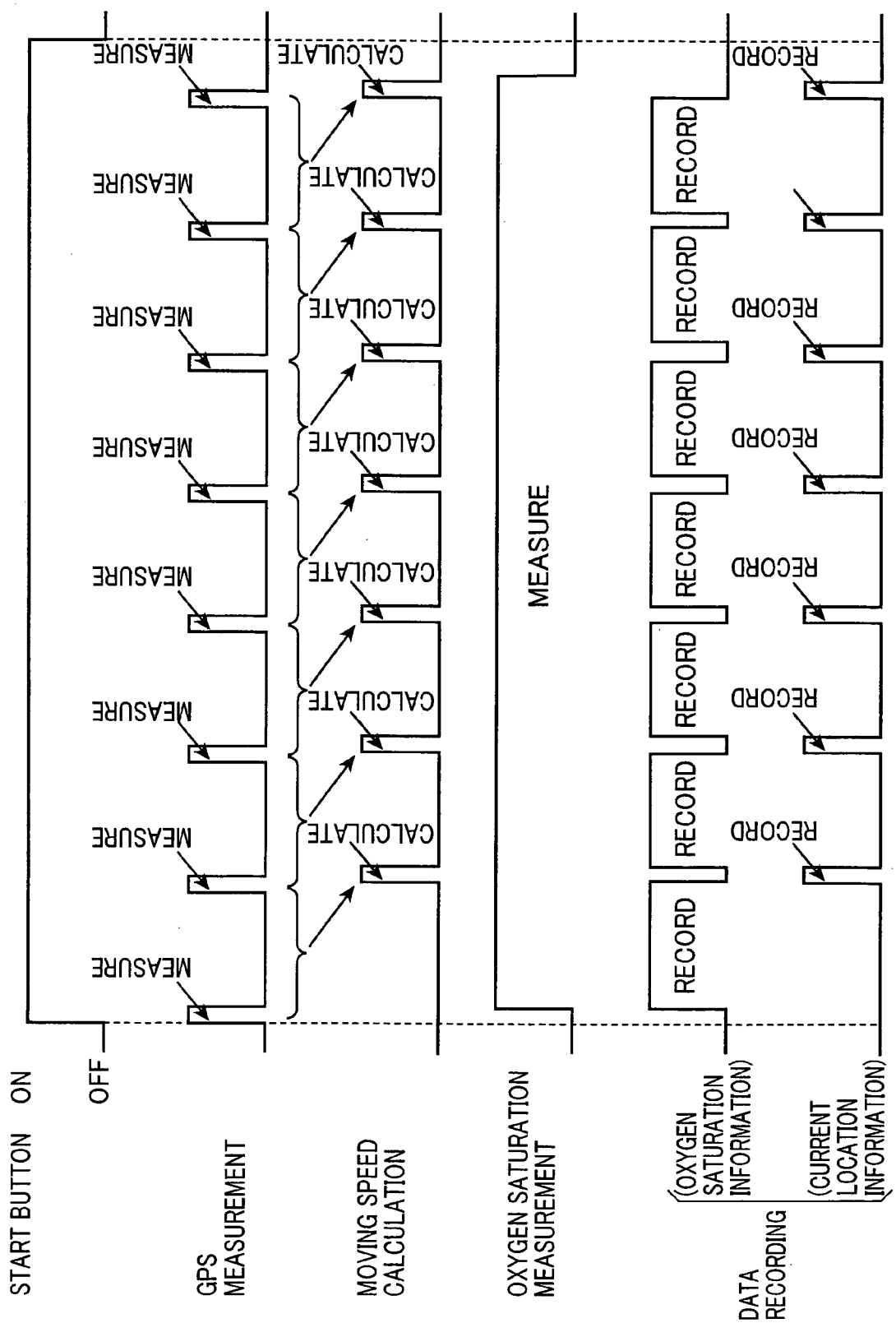
FIG. 21 is a time chart showing execution timing of the measuring operations performed by the biometric information measuring apparatus of the sixth embodiment of the invention.

A biometric information measuring apparatus 2 according to the sixth embodiment is configured to calculate moving speed of the biometric information measuring apparatus 2 (or the subject equipped with the biometric information measuring apparatus 2) from information on the current location acquired by the GPS block 25 and store measured biometric information in association with the calculated moving speed. FIG. 20 is a flowchart showing a sequence of measuring operations performed by the biometric information measuring apparatus 2 of the sixth embodiment, and FIG. 21 is a time chart showing execution timing of the measuring operations performed by the biometric information measuring apparatus 2 of the sixth embodiment, FIG. 21 including, from top to bottom, ON/OFF states of the start button, measuring cycles of the GPS block 25, moving speed calculation cycles, oxygen saturation measuring cycles and data recording cycles.

When the subject presses the start button (Yes in step #81), the control block 18 causes the GPS block 25 to perform operation for measuring the current location in step #82 and the biometric information measuring apparatus 2 to perform operation for measuring the oxygen saturation in step #83. The control block 18 of the biometric information measuring apparatus 2 of this embodiment is provided with an unillustrated timer for counting time. Upon completion of the oxygen saturation measuring operation of step #83, the timer begins to count time in step #84.

In succeeding step #85, the control block 18 judges whether the timer has counted a specified period of time. If the control block 18 judges that the specified period of time has not been counted yet (No in step #85), the control block 18 remains waiting in step #85. If the control block 18 judges that the specified period of time has been counted (Yes in step #85), the control block 18 causes the GPS block 25 to perform the operation for measuring the current location again in step #86. Then, the control block 18 resets and restarts the timer in step #87.

It is possible to calculate the moving speed of the biometric information measuring apparatus 2 from two locations thereof most recently measured by the GPS block 25 and measuring intervals of the GPS block 25. As the measuring intervals of the GPS block 25 defined by the counting time period of the timer are known, the control block 18 can calculate the moving speed of the biometric information measuring apparatus 2 between the aforementioned two locations of the biometric information measuring apparatus 2.

Proceeding to step #88, the control block 18 calculates the moving speed of the biometric information measuring apparatus 2 between the two latest locations of the biometric information measuring apparatus 2 measured by the GPS block 25. Then, the control block 18 causes the biometric information measuring apparatus 2 to store information on the oxygen saturation measured between the two locations in association with information on the moving speed of the biometric information measuring apparatus 2 in the storage device 20 in step #89.

In succeeding step #90, the control block 18 judges whether the stop button has been pressed. If the stop button has not been pressed yet (No in step #90), the control block 18 returns to step #85. If the stop button has been pressed (Yes in step #90), on the other hand, the control block 18 terminates execution of the sequence of FIG. 20.

Since the biometric information measuring apparatus 2 of this embodiment is configured to calculate the moving speed thereof from the information on the current location acquired by the GPS block 25 as discussed above, the biometric information measuring apparatus 2 can provide the medical expert, for instance, with information on physical activity level (e.g., walking, running, moving speed) of the subject at the time of oxygen saturation measurement, making it possible to analyze a relationship between the physical activity level of the subject and the biometric information. Therefore, the medical expert, for instance, can properly analyze the biometric information in consideration of the physical activity level of the subject.

While the preferred embodiments of the invention have thus far been described, the aforementioned arrangements of the embodiments may be modified in various ways. Described below are some examples of such modifications.

Figure 22:
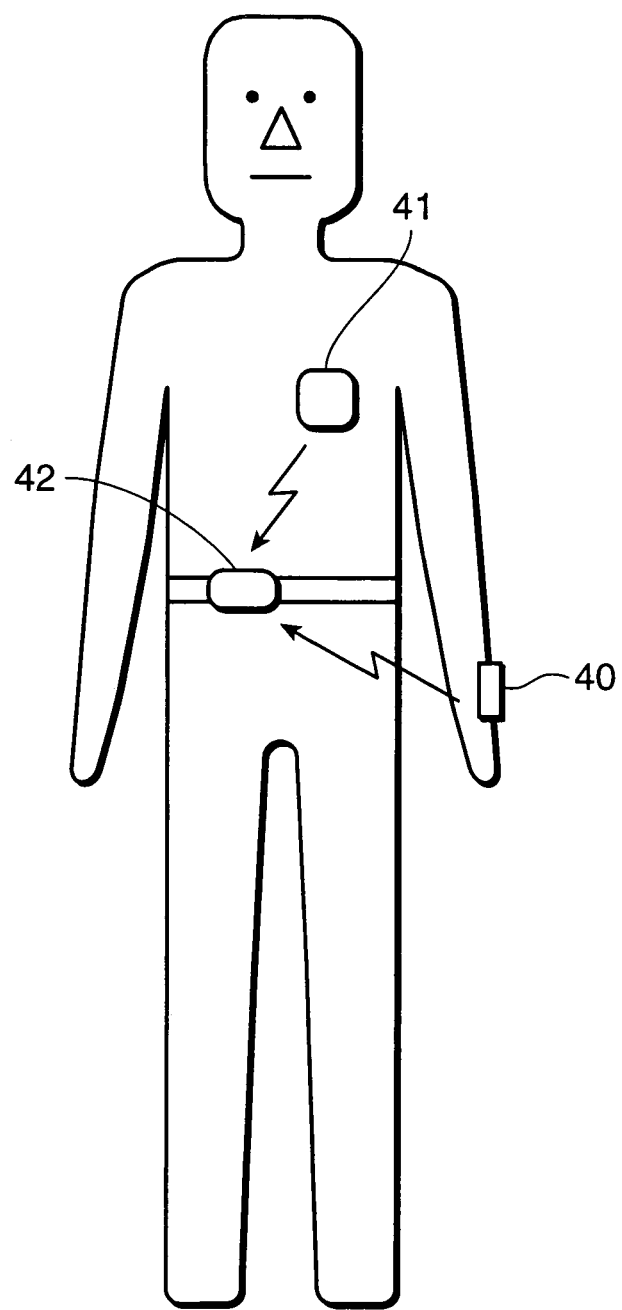
FIG. 22 is a diagram showing a variation of the biometric information measuring apparatus of the foregoing embodiments of the invention.

While the GPS block 25 is built in the main unit 4 of the biometric information measuring apparatus 2 in the foregoing embodiments, the invention is not limited to this arrangement. A biometric information measuring apparatus 2 may be made up of separate measuring units 40, 41 for measuring plural kinds of biometric information and a GPS unit 42 for measuring the current location which are communicatably interfaced by radio as shown in FIG. 22, in which the measuring unit 40 is a pulse oximeter and the measuring unit 41 is an electrocardiograph, for example. In this configuration, the aforementioned storage device 20 is provided in the GPS unit 42 so that the measuring units 40, 41 transmit data obtained by respective measuring operations to the GPS unit 42 by radio and the GPS unit 42 stores the received data in association with information on the current location acquired by the GPS unit 42 in the internal storage device 20.

While the GPS block 25 determines the current location of the biometric information measuring apparatus 2 in latitude and longitude by using the radio waves transmitted from the plurality of artificial satellites in the foregoing embodiments, the invention is not limited to this arrangement. For example, the biometric information measuring apparatus 2 may employ such a positioning system that determines the current location of the biometric information measuring apparatus 2 within a limited area of coverage, such as an indoor area of a particular hospital or a private residence of the subject. The positioning system for determining the current location of the subject equipped with the biometric information measuring apparatus 2 within the indoor area of the subject's private residence, for instance, may be configured to include a plurality of integrated circuit (IC) tags mounted at appropriate cites in the indoor area, the IC tags storing data which allows identification of the individual cites, and an IC tag reader installed in the biometric information measuring apparatus 2. The biometric information measuring apparatus 2 thus configured determines the current location of the subject based on information concerning identification of one of the IC tags read by the IC tag reader.

The biometric information which may be measured by the biometric information measuring apparatus 2 of the foregoing embodiments is not limited to the oxygen saturation but may include such parameters as irregular heart rate, vascular age, state of sleep, blood pressure, brain waves, body temperature, state of jaundice and symptoms related to sleep apnea syndrome. Thus, the biometric information measuring apparatus 2 may be configured to serve as an electrocardiograph, a blood pressure gauge, a clinical thermometer and/or a jaundice meter for measuring the aforementioned parameters, in addition to the pulse oximeter.

While the main unit 4 and the sensor unit 6 of the biometric information measuring apparatus 2 of the foregoing embodiments are connected by the cable 5 as illustrated in FIG. 1, the invention is not limited to this arrangement. Instead, the biometric information measuring apparatus 2 may be modified such that the main unit 4 and the sensor unit 6 are communicatably connected by wireless networking using an infrared communications link designed according to the Bluetooth specification, for example.

The invention is not limited to an arrangement in which the PC 3 displays the current location obtained by the GPS block 25 in latitude and longitude alone on the display unit 12. For example, the PC 3 may graphically present the current location of the biometric information measuring apparatus 2 superimposed on a map displayed on the display unit 12.

This specification discloses various embodiments as described above. The primary embodiments are summarized as follows.

In one aspect of the invention, a biometric information measuring apparatus according to a principal feature of the invention that is attached to a living body for acquiring specific biometric information thereof comprises a sensing portion for detecting a biometric signal representative of the biometric information, a processing portion for deriving biometric information data from the biometric signal detected by the sensing portion, a positioning portion for acquiring position information indicating the current location of the sensing portion by use of radio waves, and a storage portion for storing one of the biometric signal detected by the sensing portion and the biometric information data derived by the processing portion in association with the position information acquired by the positioning portion.

The biometric information measuring apparatus thus configured stores the position information indicating the current location of the sensing portion and the biometric signal or the biometric information data concerning the biometric information in association with each other in the storage portion. Thus, the biometric information measuring apparatus can provide the biometric signal or the biometric information data together with the position information acquired when the biometric signal or the biometric information data was obtained. Since the biometric information measuring apparatus provides a medical expert (or subject) with information on the state of the subject, such as his or her location, behavior and ambient conditions, at a point in time when the biometric signal or the biometric information data was obtained, the medical expert or the subject is allowed to conduct a precise analysis of the biometric information concerning the subject in consideration of the location and behavior of the subject at the time of measurement. The sensing portion, the processing portion, the positioning portion and the storage portion of the apparatus may be integrated into a single unit or configured as separate units.

In another aspect of the invention, the biometric information measuring apparatus further comprises a controller which instructs the positioning portion to perform operation for acquiring the position information, so that the positioning portion acquires the position information as instructed by the controller.

Since the biometric information measuring apparatus according to this aspect of the invention includes the controller for instructing the positioning portion to perform the operation for acquiring the position information, it is possible to cause the biometric information measuring apparatus to automatically acquire the position information.

In another aspect of the invention, the controller causes the positioning portion to repeatedly perform the operation for acquiring the position information during a period of time when the sensing portion continues to detect the biometric signal, and the controller causes the storage portion to store the position information in association with one of the biometric signal and the biometric information data generally in synchronism with the operation for acquiring the position information.

According to this aspect of the invention, the positioning portion repeatedly acquires the position information during the period of time when the sensing portion continues to detect the biometric signal and the storage portion stores each piece of position information in association with the biometric signal or the biometric information data generally in synchronism with the operation for acquiring the position information. The biometric information measuring apparatus thus configured can provide the position information indicating the current location of the sensing portion at each point in time when the biometric signal or the biometric information data is obtained.

In another aspect of the invention, the biometric information measuring apparatus further comprises an operating portion which is operated when instructing the storage portion to store position information indicating a location to be preregistered, and a decision portion for judging whether the position information acquired by the positioning portion matches the position information indicating the preregistered location. In this biometric information measuring apparatus, the controller causes the sensing portion to detect the biometric signal when the decision portion judges that the acquired position information matches the position information indicating the preregistered location, and the controller causes the storage portion to store the position information judged to match the position information indicating the preregistered location in association with one of the biometric signal and the biometric information data.

In the biometric information measuring apparatus thus configured, the sensing portion detects the biometric signal when the position information acquired by the positioning portion matches the position information indicating the location preregistered in the storage portion, and the storage portion stores the position information acquired by the positioning portion in association with the biometric signal or the biometric information data obtained when the decision portion judges that the acquired position information matches the position information indicating the preregistered location. According to this aspect of the invention, the biometric information measuring apparatus provides only such data concerning the biometric signal or the biometric information that is obtained at a specified (preregistered) measuring cite, making it possible to properly analyze the biometric signal or the biometric information, whichever provided.

In another aspect of the invention, the controller causes the positioning portion to perform the operation for acquiring the position information when one of the biometric signal and the biometric information data goes into a predefined state.

In the biometric information measuring apparatus thus configured, the positioning portion is caused to perform the operation for acquiring the position information when the biometric signal or the biometric information data goes into the predefined state (e.g., a predefined abnormal state) and the storage portion is caused to store the acquired position information in association with the biometric signal or the biometric information data which has gone into the predefined state. Since the biometric information measuring apparatus provides information on the state of the subject, such as his or her location, behavior and ambient conditions, at a point in time when the biometric signal or the biometric information data has gone into the predefined state, the medical expert or the subject can properly analyze the biometric signal or the biometric information data in consideration of the state of the subject.

In another aspect of the invention, the sensing portion has capability to detect biometric signals representative of plural kinds of biometric information, the storage portion stores in advance a relationship between the plural kinds of biometric information and locations where the biometric signals representative of the respective kinds of biometric information should be detected, and the controller specifies at least one kind of biometric information and causes the sensing portion to detect the biometric signal representative of the specified kind of biometric information when the current location indicated by the position information acquired by the positioning portion matches the location where the biometric signal representative of the specified kind of biometric information should be detected.

In the biometric information measuring apparatus thus configured, the controller specifies at least one kind of biometric information and causes the sensing portion to detect the biometric signal representative of the specified kind of biometric information when the current location indicated by the position information acquired by the positioning portion matches the location where the biometric signal representative of the specified kind of biometric information should be detected. Then, the storage portion stores the biometric signal or the biometric information data in association with the kind of biometric information. Thus, the biometric information measuring apparatus according to this aspect of the invention can acquire the biometric signals or the biometric information data appropriate for plural measuring cites. Since the biometric information measuring apparatus provides the biometric signals or the biometric information data appropriate for the individual measuring cites, the medical expert or the subject can properly analyze each kind of biometric signals or biometric information data obtained.

In another aspect of the invention, the controller causes the positioning portion to repeatedly perform the operation for acquiring the position information during a period of time when the sensing portion continues to detect the biometric signal, the controller calculates moving speed of the sensing portion from the distance between locations where the positioning portion acquires first position information and second position information while the sensing portion detects the biometric signal and a time difference between points in time when the positioning portion acquires the first position information and the second position information, and the controller causes the storage portion to store information on the moving speed of the sensing portion in association with one of the biometric signal and the biometric information data obtained during a period of time when the first position information and the second position information were acquired.

In the biometric information measuring apparatus thus configured, the controller calculates the moving speed of the sensing portion between two locations where the positioning portion acquires the first position information and the second position information from the distance between the two locations and the time difference between the points in time when the first position information and the second position information are acquired while the biometric information is being acquired, and the storage portion stores the information on the moving speed of the sensing portion in association with the biometric signals or the biometric information data obtained during the points in time when the first position information and the second position information were acquired. This arrangement makes it possible to analyze a relationship between physical activity level of the subject and the biometric signals or the biometric information data obtained. Accordingly, the medical expert or the subject can properly analyze the biometric signals or the biometric information data in consideration of the physical activity level of the subject.

In another aspect of the invention, a biometric information measuring system comprises a biometric information measuring unit attached to a living body for acquiring specific biometric information thereof, and an analyzing unit for analyzing the biometric information. The biometric information measuring unit includes a sensing portion for detecting a biometric signal representative of the biometric information, a processing portion for deriving biometric information data from the biometric signal detected by the sensing portion, a positioning portion for acquiring position information indicating the current location of the sensing portion by use of radio waves, and a storage portion for storing one of the biometric signal detected by the sensing portion and the biometric information data derived by the processing portion in association with the position information acquired by the positioning portion. The analyzing unit includes an analyzing portion for analyzing one of the biometric signal and the biometric information data and the position information stored in association with each other in the storage portion according to predefined content of analysis, and a display portion for displaying results of analysis obtained by the analyzing portion.

In the biometric information measuring system thus configured, the analyzing unit interfaced to the biometric information measuring unit can provide the results of analysis of the biometric signals or the biometric information data and the position information stored in the storage portion. Since the biometric information measuring system notifies the medical expert or the subject of the results of analysis of the biometric signals or the biometric information data and the position information obtained in accordance with the predefined content of analysis, the medical expert or the subject can properly diagnose the biometric information and take necessary action, if any.

While the invention has thus far been described in detail with reference to the preferred embodiments thereof and the accompanying drawings, various modifications and alterations of the aforementioned arrangements of the embodiments would be obvious to those skilled in the art. It should therefore be understood that the invention is intended to cover all such modifications and alterations as long as these modifications and alterations fall within the spirit and scope of the invention which are determined solely by the appended claims.

What is claimed is:

1. A pulse oximeter attached to a living body for acquiring an arterial oxygen saturation as biometric information thereof, said pulse oximeter comprising:
    a sensing portion for detecting a biometric signal representative of the arterial oxygen saturation;
    a processing portion for deriving oxygen saturation information from the biometric signal detected by said sensing portion;
    an analyzing portion for analyzing one of the biometric signal and the oxygen saturation information data;
    a positioning portion for acquiring position information indicating the current location of said sensing portion by use of radio waves;
    a storage portion for storing one of the biometric signal detected by said sensing portion and the oxygen saturation information derived by said processing portion;
    a controller configured to instruct said position portion to perform an operation of acquiring the position information at a specified time interval during measurement of the oxygen saturation, and
    wherein the controller is further configured to cause the sensing portion to detect the biometric signal and the storage portion to store the biometric signal or the oxygen saturation information in association with the position information when the current location acquired by the positioning portion matches a predefined site.

2. The pulse oximeter apparatus according to claim 1, wherein
    said controller causes said positioning portion to repeatedly perform the operation of acquiring the position information during a period of time when said sensing portion continues to detect the biometric signal,
    said controller calculates a moving speed of said sensing portion from the distance between locations where said positioning portion acquires first position information and second position information while said sensing portion detects the biometric signal and a time difference between points in time when said positioning portion acquires the first position information and the second position information, and
    said controller causes said storage portion to store information on the moving speed of said sensing portion in association with one of the biometric signal and the oxygen saturation information obtained during a period of time when the first position information and the second position information were acquired.

3. The pulse oximeter according to claim 1, wherein the sensing portion comprises a light emitter and a light sensor.

4. The pulse oximeter according to claim 3, wherein the light emitter comprises a first light-emitting diode for emitting red light having a first wavelength in red light range, and a second light-emitting diode for emitting infrared light having a second wavelength in infrared light range.

5. The pulse oximeter according to claim 1, wherein the biometric signal representative of the arterial oxygen saturation is a photoplethysmographic signal.

6. The pulse oximeter according to claim 1, wherein the processing portion is structured to further derive heart rate information from the biometric signal detected by the sensing portion.

7. A pulse oximeter system comprising:
- a pulse oximeter unit attached to a living body for acquiring an arterial oxygen saturation as biometric information thereof; and
- an analyzing unit for analyzing the arterial oxygen saturation as the biometric information;

wherein said pulse oximeter unit includes:
- a sensing portion for detecting a biometric signal representative of the arterial oxygen saturation;
- a processing portion for deriving oxygen saturation information from the biometric signal detected by said sensing portion;
- a positioning portion for acquiring position information indicating the current location of said sensing portion by use of the Global Positioning System (GPS) at a specified time interval during measurement of the oxygen saturation; and
- a storage portion for storing one of the biometric signal detected by said sensing portion and the oxygen saturation information derived by said processing portion in association with the position information most recently acquired by said positioning portion;
- a controller configured to cause the sensing portion to detect the biometric signal and the storage portion to store the biometric signal or the oxygen saturation information in association with the position information when the current location acquired by the positioning portion matches a predefined site; and
- a display portion for displaying results of analysis obtained by said analyzing portion.

* * * * *